United States Patent
Bae et al.

(10) Patent No.: US 6,589,567 B2
(45) Date of Patent: *Jul. 8, 2003

(54) ANTI-CANCER THERAPY AGENT OF ARSENIC HEXOXIDE ($AS_4O_6$) OF A NATURAL CHEMICAL SUBSTANCE AND ITS PHARMACEUTICAL COMPOSITION

(75) Inventors: Ill-Ju Bae, 24-5, 393-86, Daebang-dong, Tongjak-ku, Seoul (KR); Jong-Bae Kim, Pohang (KR); Choong-Ki Eun, Pusan (KR); Seung-Kyu Song, Pohang (KR); Byung-Sun Suh, Pohang (KR); Kwan-Hee Lee, Pohang (KR); Myoung-Sool Doo, Pohang (KR); Jin-Hwan Kwak, Pohang (KR); Byung-Doo Song, Pohang (KR); Taek-Joon Yoon, Koyang (KR); Tae-Bong Kang, Pohang (KR); Choon-Ho Park, Pohang (KR)

(73) Assignee: Ill-Ju Bae, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 09/951,393

(22) Filed: Sep. 14, 2001

(65) Prior Publication Data

US 2002/0028253 A1 Mar. 7, 2002

Related U.S. Application Data

(63) Continuation of application No. 09/105,086, filed on Jun. 26, 1998.

(30) Foreign Application Priority Data

May 8, 1998 (KR) .............................. 98-16486

(51) Int. Cl.[7] .............................. A01N 59/22
(52) U.S. Cl. ..................................... 424/623
(58) Field of Search ......................... 424/623

(56) References Cited

PUBLICATIONS

Kehri et al., Natl. Acad. Sci. Lett. (India) (1986), 9(10), 301–2 Abstract Only.*

* cited by examiner

Primary Examiner—Jerome D. Goldberg
(74) Attorney, Agent, or Firm—Gary M. Nath; Todd L. Juneau; Joshua B. Goldberg

(57) ABSTRACT

This invention is about the identification of the HD-2, a natural chemical substance that was separated and purified from a natural product, Sinsuk, as arsenic hexoxide ($As_4O_6$) and about its therapeutic efficacy as an anti-cancer drug and pharmaceutical composition.

Arsenic hexoxide ($As_4O_6$), a natural chemical substance obtained from Sinsuk after eliminating the toxic property, has a potent anti-cancer efficacy by its direct cytotoxicity on tumor cells and suppresses the formation of new blood vessels of tumor masses, which results in complete cure of malignant cancers.

1 Claim, 34 Drawing Sheets

Lanes
1 : DNA size marker
2 : negative control, only medium
3 : HD-2 50μg/ml
4 : HD-2 25μg/ml
5 : HD-2 10μg/ml
6 : HD-2 5μg/ml
7 : positive control, cisplatin 20μg/ml

ANTI-CANCER THERAPY AGENT OF ARSENIC HEXOXIDE ($AS_4O_6$) OF A NATURAL CHEMICAL SUBSTANCE AND ITS PHARMACEUTICAL COMPOSITION This application is a continuation application of U.S. patent application Ser. No. 09/105,086 filed Jun. 26, 1998, the contents of which are hereby incorporated by reference in their entirety.

FIELD OF THE INVENTION

The present invention relates to the identification of HD-2, a natural chemical substance that was separated and purified from a natural product, Sinsuk, as arsenic hexoxide ($As_4O_6$) and about its therapeutic efficacy as an anti-cancer drug and pharmaceutical composition, and more particularly, to the purification processes of a natural chemical substance (arsenic hexoxide, $As_4O_6$) from Sinsuk while eliminating the toxicity and the novel anti-cancer effect of $As_4O_6$ and its pharmaceutical composition by their direct cytotoxicity and suppression of new angiogenesis at and around tumor sites.

BACKGROUND OF THE INVENTION

In general, various drugs are presently available for anti-cancer chemotherapy. Alkylating agents, such as cisplatin and cyclophosphamide, manifest their anti-cancer effect by forming covalent bonds with nitrogen atoms of DNA nucleotides because of its highly electrophilic property of the active site. Antimetabolites, such as 5-fluorouracil, act by inhibiting enzymes involved in biosynthesis of nucleic acids or by being inserted into DNA or RNA structures by itself. Some antibiotics, such as adriamycin, act potently on DNA to inhibit the normal function, which results in suppression of tumor growth. But all of these anti-cancer agents affect not only pathological tumor cells, but also normal healthy cells, especially bone marrow cells or intestinal epithelia with high turnover rate, which cause serious complications and toxicity, such as myelosuppression, alopecia, renal failure, nausea and vomiting, neurotoxicity, etc.

On the other hand, arsenic has been known as a potent, environmental carcinogen, affecting skin and lung often. Arsenic is reported to bind to sulfohydryl structure of enzymes to inactivate target enzymes, to inhibit phosphorylation and dephosphorylation reactions, which are vital for regulation of enzyme activities, and to cause abnormalities in chromosomes. Therefore arsenic has been studied mostly from toxicological aspect, related to these reports up to now.

But in the past, arsenic had been used as a therapeutic agent in both Oriental and Occidental medicines. Especially, in traditional Chinese medicine including Korean medicine, arsenic compound had been prescribed for a long time to treat some fatal diseases, e.g. to eradicate evil energy. In old medical literatures of Korea and China, it is described that arsenic was prescribed as a medicine by the name of Eungwhang in page 1234 or by the name of Bisang in page 1237 of TonEuiBoGam (NamSaDang), or Encyclopedia of Oriental Medicine, where it is described that arsenic was prescribed only after reducing its toxicity, because of its extreme toxicity. Also arsenic was known to have detoxifying activity against several toxic substances. For example, arsenic was used in managing choongak, or vomiting and in eradicating spirits and evil energy. In an old literature of Chinese medicine (BonChoKangMok (Encyclopedia of Herbs of Chinese Medicine), pages 12–16 of vol. 9), indications and pharmacological actions of arsenic (by the name of whangwoong) are described, where arsenic is reported to have the action of purifying the blood. Thus arsenic had been recognized as an active medicine and used for a long time, but in Korea, arsenic is recognized as a possibly harmful chemical with characteristics of heavy metals and accordingly its use is quite limited. Arsenic possesses some characteristics of heavy metals although it does not belong to heavy metal group and therefore, has been avoided in the production of medicine. Exposure to arsenic leads to anemia, leukopenia, and dysfunction of kidney and liver and chronic exposure may have carcinogenic effect.

In Western medicine, arsenic compound was prescribed for treating several diseases, including rheumatism, syphilis, psoriasis, etc. and low dose of arsenic compound had been known to have beneficial effect on physiological functions of human body, including stimulation of hematopoiesis, which coincides with descriptions in old literatures of Oriental medicine. But in modern medicine, indications for arsenic compound became very limited. From the end of 19th century to the beginning of 20th century, arsenic compound was tried to treat chronic leukemia and after 1950s, melarsoprol, an organic compound of arsenic which was prescribed for African trypanosomiasis, is the only arsenic compound in use at present time.

Based on these pharmacological properties of arsenic, attempts have been made recently to develop a novel anti-cancer drug and presently some studies are making rapid progress in this field. After the Cultural Revolution, China has been putting considerable efforts to study traditional medicine using the scientific tools of Western medicine. They published a report in 1996, in collaboration with a French research team, that arsenic trioxide ($As_2O_3$) had an excellent effect in treating acute promyelocytic leukemia. Researchers of Western medicine were marveled at this result, because arsenic trioxide was especially effective in treating leukemia patients who had been resistant to conventional chemotherapy since this paper was published, more medical scientists of Western Hemisphere became interested in the possible anticancer effect of arsenic compounds. Stimulated by these results, considerable efforts have been made to integrate traditional Oriental Medicine and modern molecular medicine by interpreting the results of Oriental Medicine in terms of mainstream modern anti-cancer chemotherapy. It is extremely important to develop novel chemicals to have effective anticancer efficacy without any serious side effects. The invention described here succeeded in the separation and purification of the active ingredient by treating a natural, raw material of arsenic, which had been used in Oriental medicine, through multiple processes. Additionally clinical study indicated that pharmaceutical composition of arsenic hexoxide shows potent anticancer efficacy without any obvious side effects.

SUMMARY OF THE INVENTION

Accordingly, the present invention is to provide a novel, natural chemical substance, arsenic hexoxide ($As_4O_6$) obtained from Sinsuk, while eliminating toxicity.

The other object of this invention to elucidate the action mechanism of anticancer efficacy of the novel, natural chemical substance obtained from Sinsuk.

Another object of the invention is to describe the usage of the novel, natural chemical substance for anticancer therapy and its pharmacological composition.

To achieve these advantages in accordance with the purpose of the present invention, as embodied and broadly described, first we separated and purified a natural chemical substance, HD-2, by repeated heating of Sinsuk containing arsenic to eliminate the toxicity, which was followed by structure analysis. The white substance obtained by this procedure was tested on cloned tumor cells of mice and human beings, to evaluate the anticancer efficacy of the substance and to see whether the anticancer effects are caused by tumor cell death by apoptosis mechanism. Toxicity of HD-2 following acute administration was evaluated by observing clinical symptoms of rats after a single, oral administration of a large dose and The toxicity of HD-2 following subacute administration was evaluated by observing clinical symptoms of rats after a slow oral administration. Clonal tumor cells, targeted to lungs, were injected intravenously into mice and HD-2 was administered orally or through intravenous route. Afterward the number of metastatic tumor masses in Lungs was counted to evaluate the inhibitory effect of the substance on cancer metastasis. Similarly, melanoma cells were inoculated intradermally into mice, followed by oral administration of HD-2, after which anticancer mechanism of HD-2 was investigated by counting the number of new blood vessels formed at or around tumor masses. Cancer was induced by injection of carcinogen into mice and tumor-suppressing efficacy was measured in these mice after oral administration of HD-2. We also tested a pharmacological composition prepared by mixing various herbs of Chinese medicine with arsenic hexoxide, which was administered orally to cancer patients at terminal stage to evaluate the anticancer efficacy.

In accordnace with one aspect, the present invention provides an anti-cancer agent of arsenic hexoxide ($As_4O6$) of a natural chemical substance and its pharmaceutical composition comprising:

1) We separated and purified a natural chemical substance of white color, HD-2, by repeated heating of Sinsuk containing arsenic and arsenic of reagent grade, which were followed by structure analysis to show that it corresponds to arsenic hexoxide, $As_4O_6$.
2) A natural chemical substance, $As_4O_6$, obtained by this procedure was added to culture media to grow cloned tumor cells of mice and human beings, to evaluate the anticancer efficacy of the substance.
3) The anticancer mechanism of $As_4O_6$ was studied to examine whether the anticancer efficacy was due to tumor cell death by apoptosis mechanism.
4) Different amounts of a natural chemical substance, $As_4O_6$, was acutely administered orally to male and female rats, to examine the acute toxicity of arsenic hexoxide by observing manifested complications.
5) Same amount of a natural chemical substance, $As_4O_6$, was slowly administered orally to male and female rats, to examine the subacute toxicity of the invention by observing manifested complications.
6) Clonal tumor cells, targeted to lungs, were injected intravenously into mice and a natural chemical substance, $As_4O_6$, was administered orally or through intravenous route. Afterwards the number of metastatic tumor masses appearing in lungs was counted to evaluate the inhibitory effect of the substance on cancer metastasis.
7) Similarly, malignant melanoma cells were inoculated intradermally into mice followed by oral administration of a natural anticancer agent, $As_4O_6$. Afterwards anticancer mechanism was studied by measuring the size of tumor masses and by counting the number of newly formed blood vessels at and around tumor masses.
8) Carcinogen was injected into mice to induce malignant tumors and anticancer effects of a natural anticancer agent, $As_4O_6$, were studied by measuring the incidence and size of tumors in liver and lung.
9) We also prepared pharmaceutical composition by adding various herbs of Oriental medicine to a natural anticancer agent, $As_4O_6$, in several forms (tablet, capsule, and solution).
10) Tablets prepared as described above were administered orally to cancer patients at terminal stage, carrying a malignant cancer of uterus, lung, maxillary sinus, kidney, or urinary bladder, to evaluate the therapeutic efficacy of $As_4O_6$. The size of the tumors and clinical courses were monitored using computed tomography (CT) and magnetic resonance imaging (MRI).

It is to be understand that both the forgoing general description and the following detailed description are exemplary and explanatory and are intended to provide further explanation of the invention as claimed.

BRIEF DESCRIPTION OF THE ATTACHED DRAWINGS

The accompaned drawings, which are included to provide a further understanding of the invention and are incorporated in and constitute a part of this specification, illustrate embodiments of the invention and together with the description serve to explain the principles of the drawings:

DETAILED DESCRIPTION OF THE PREFERRED EMBODIMENT

Reference will now be made in detail to the preferred embodiments the present invention, examples of which are illustrated in the accompanied drawings.

EXAMPLE 1

Separation and Purification of a Natural Chemical Substance, HD-2

Mixture of 10-g Sinsuk and 10-ml ethanol ($C_2H_5OH$) was heated for 1 hour and then, cooled to room temperature for 1 hour. Another volume of 10-ml ethanol was added to cooled Sinsuk and the sequential heating and cooling were repeated several times. The product of this procedure was washed in 20-ml distilled water with 10-min stirring and shaking for 10 min, and 2-ml of distilled water was added to it. 1 min later, precipitates were collacted-by decanting. This collection process was repeated three times. After storing the washed precipitates at −40° C. for 24 hours, precipitates were defrosted and poured onto a filter paper and were dried at room temperature. 9 grams of white substance was obtained as a purified final product.

Figure 1:
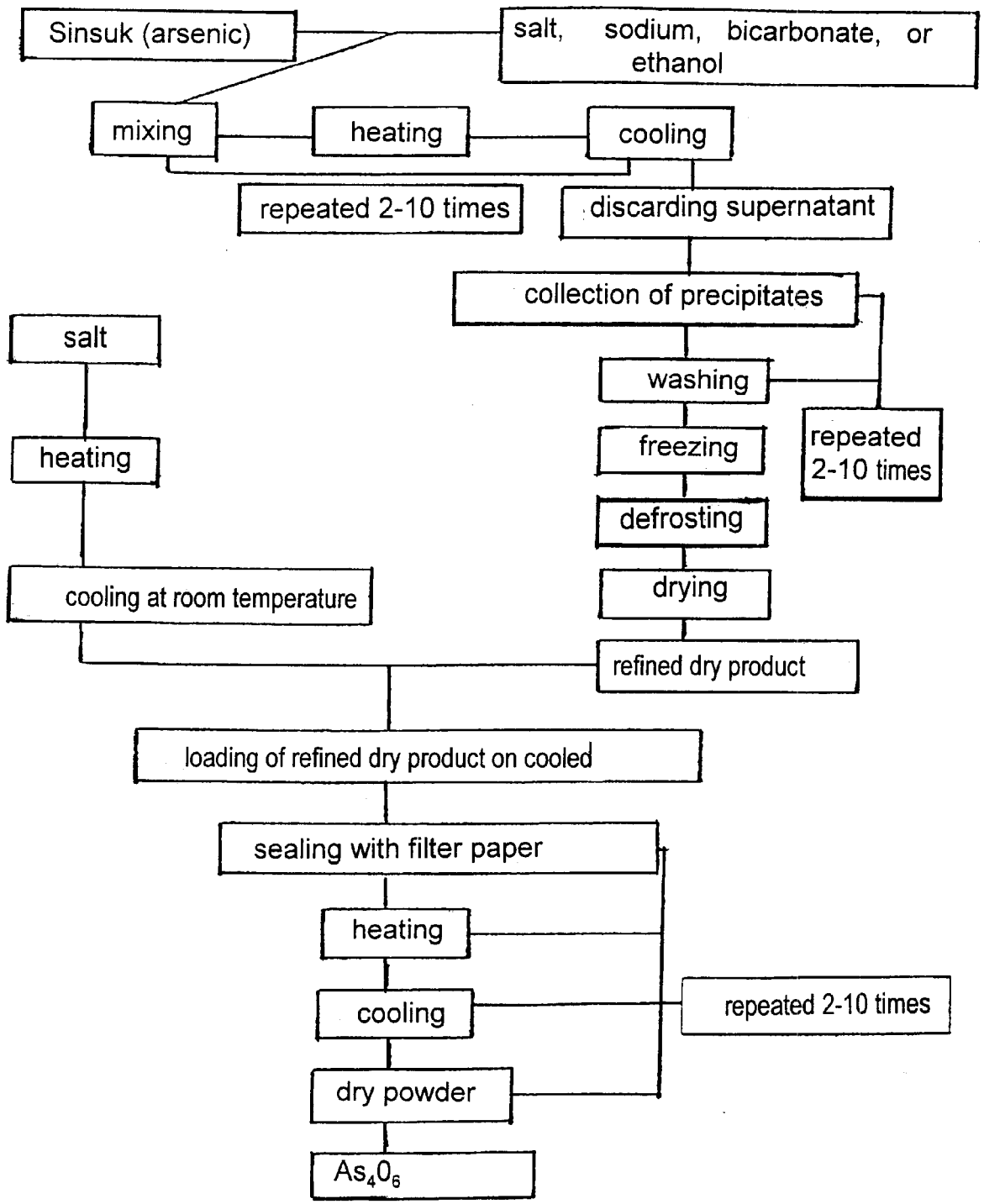
FIG. 1 shows schematized procedures for separation and chemical purification of Sinsuk.

The white substance was further purified for detoxification. Salt was placed in a china made of Kaolin and heated to remove water component. After cooling at room temperature, the white substance was placed on the top of the salt and sealed with a filter paper and heated over 1 hour. After cooling at room temperature, the white substance was collected. This process was repeated more than 2 times. Finally 2 grams of a white substance was obtained, which was named as HD-2 (see FIG. 1).

EXAMPLE 2

Structural Analysis of a Natural Chemical Substance, HD-2

White substance obtained in EXAMPLE 1 was sent to Korean Institute of

Figure 2:
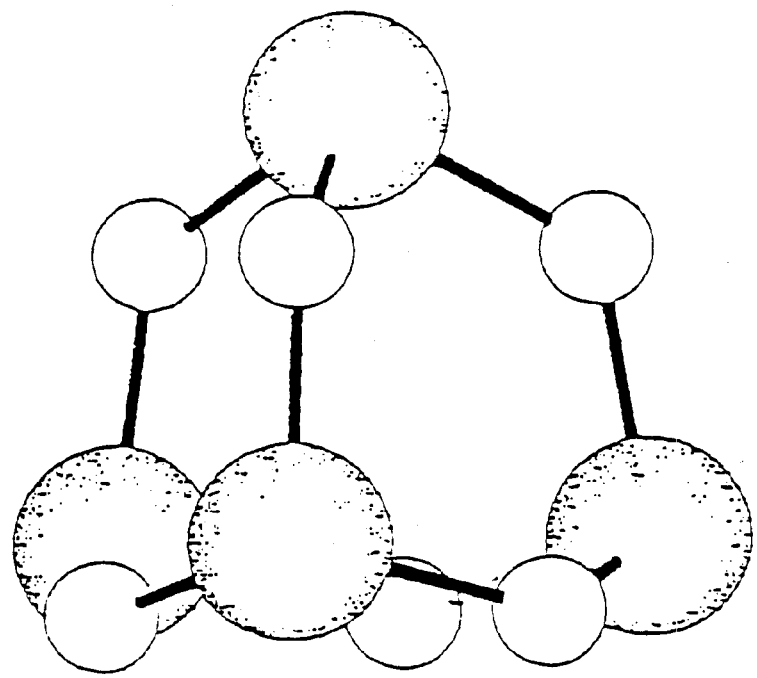
FIG. 2 shows the 3-dimensional structure model of Sinsuk determined by structure analysis.
Figure 2:
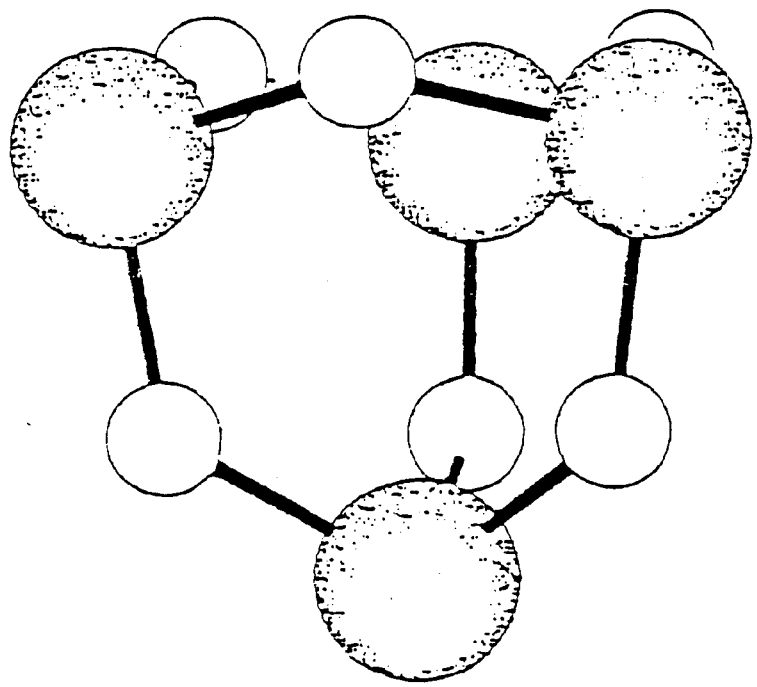

White substance obtained in EXAMPLE 1 was sent to Korean Institute of Science and Technology for the structural analysis, where it was identified as a substance with an empirical formula of $As_4O_6$ with 3-dimensional structure shown in FIG. 2. Physical and chemical parameters of $As_4O_6$ are summarized in Table 1. Atomic coordinates ($\times 10^4$) and equivalent isotropic displacement parameters. ($Å^2 \times 10^3$) are listed in Table 2, bond lengths (A) and bond angles (degree) in Table 3, and anisotropic displacement parameters in Table 4.

TABLE 1

Crystal data and structure refinement of $As_4O_6$

| parameters | |
|---|---|
| Empirical formula | $As_4O_6$ |
| Formula weight | 395.68 |
| temperature | 293(2)K |
| wave length | 0.71073A |
| Crystal system | cubic |
| Space group | Fd3barm |
| Unit cell dimensions | a = 11.0457(11)A  alpha = 90 deg |
| | b = 11.046(2)A  beta = 90 deg |
| | c = 11.0457(10)A  gamma = 90 deg |
| Volume | 1347.7(3) $A^3$ |
| Z | 8 |
| Density(calculated) | 3.900 $Mg/m^3$ |
| Absorption coefficient | 19.634 $mm^{-1}$ |
| F(000) | 1440 |
| Theta range for data collection | 30.98 deg at 3.19 |
| Index range | 0 <= h <=10, 0 <= k <=14, 0 <= 1 <=16 |
| Reflections collected | 319 |
| Independent reflections | 95[R(int) = 0.791] |

TABLE 1-continued

Crystal data and structure refinement of $As_4O_6$

| parameters | |
|---|---|
| Refinement method | Full-matrix least-squares on $F^2$ |
| Data/restraints/parameters | 95/0/9 |
| Goodness-of-fit on $F^2$ | 1.009 |
| Final R indices[I > 2sigma(I)] | R1 = 0.0383, wR2 = 0.1111 |
| R indices(all data) | R1 = 0.0401, wR2 = 0.1130 |
| Absolute structure parameter | 10(10) |
| Extinction coefficient | 0.0039(8) |
| Largest diff. peak and hole | 1.056 and −0.865 e. $A^{-3}$ |

TABLE 2

Atomic coordinates($\times 10^4$) and equivalent isotropic displacement parameters ($Å^2 \times 10^3$) for $As_4O_6$

| | |
|---|---|
| As—O#1 | 1.781(3) |
| As—O#2 | 1.781(3) |
| As—O | 1.781(3) |
| O—As#3 | 1.781(3) |
| O#1—As—O#2 | 98.1(3) |
| O#1—As—O | 98.1(3) |
| O#2—As—O | 98.1(3) |
| As—O—As#3 | 129(4) | symmetry transformations used to generate equivalent atoms
1 z − 1/2, −x + 1, −y + 3/2
2 y − 1/2, z, x + 1/2
3 −x + 1/2, y + 1 − 1, −z + 3/2

TABLE 3

Bond lengths [A] and angles [deg] for $As_4O_6$

| | X | Y | Z | U(eq) |
|---|---|---|---|---|
| As | 1471(1) | 6471(1) | 8529(1) | 13(1) |
| O | 2500 | 5778(6) | 7500 | 13(2) |

U(eq) is defined as one third of the trace of the orthogonalized Uij tensor

TABLE 4

Anisotropic displacement parameters($A^2 \times 10^3$) for $As_4O_6$

| | U11 | U22 | U33 | U23 | U13 | U12 |
|---|---|---|---|---|---|---|
| As | 13(1) | 13(1) | 13(1) | 2(1) | 2(1) | −2(1) |
| O | 13(3) | 14(4) | 13(3) | 0 | 5(3) | 0 |

The anisotropic displacement factor exponent takes the form: $-2pi^2$ [$h^2a^*U11 \ldots +2h\,k\,a^*b^*U12$]

EXAMPLE 3

Anticancer Effect of HD-2 on Cloned Tumor Cells in vitro

A natural chemical substance HD-2, obtained in EXAMPLE 1, was evaluated for anticancer efficacy by examining direct cytotoxicity on cloned tumor cells in vitro. Cisplatin was used as a control drug.

Experiment 1: Anticancer effect of HD-2 on cloned tumor cells of mice and human beings Cloned tumor cells of P388 leukemia, L1210 leukemia, L5178Y lymphoma, Colon26-M3.1 carcinoma, and B16-BL6 melanoma, from mice, and K562 leukemia, liver carcinoma HEP-G2, Hs578T breast cancer, AN-3-CA adenocarcinoma, DLD colon carcinoma, and HeLa epitheloid carcinoma, from human beings, were cultured in EMM, DMEM, or RMPI-1640 culture media containing 7.5% fetal bovine serum (FBS), as described in ATCC manual. After plating cloned tumor cells into test wells at a density of $1\times10^4/100$ μl, various concentrations of HD-2 and cisplatin were added to examine cytotoxicity of two substances. Tumor cells in test wells were incubated in 5% $CO_2$ incubator at 37° C. for 2 days. The anticancer efficacy of two substances are indicated as a concentration of the test substance to inhibit the growth of tumor cells by 50% ($ED_{50}$, 50% Effective Dose), compared with the growth of control tumor cells, where neither HD-2 nor cisplatin was added. The results (summarized in Table 5) indicate that direct cytotoxicity of HD-2 measured at 48 hours of incubation was 50±30 (mean±SD) times as high as cisplatin.

TABLE 5

Cytotoxic effect($ED_{50}$) on cloned tumor cells

| clone | HD-2 | cisplatin |
|---|---|---|
| murine | | |
| leukemia P388 | 0.17 | 3.58 |
| leukemia L1210 | 0.16 | 2.89 |
| lymohoma L5178Y | 0.06 | — |
| melanoma B16-BL6 | 0.12 | 4.7 |
| colon Colon26 | 0.90 | 5.6 |
| fibroblast 3T3 | 0.03 | 8.0 |
| human | | |
| leukemia K562 | 0.11 | — |
| liver carcinoma HEP-G2 | 0.07 | 5.6 |
| breast cancer Hs578T | 0.35 | — |
| adenocarcinoma AN3CA | 0.06 | — |
| colon cancer DLD-1 | 0.21 | 6.8 |
| carcinoma Hela | 0.05 | — |

Experiment 2: Anticancer effect of HD-2 in 3T3-fibroblast cells

Figure 3:
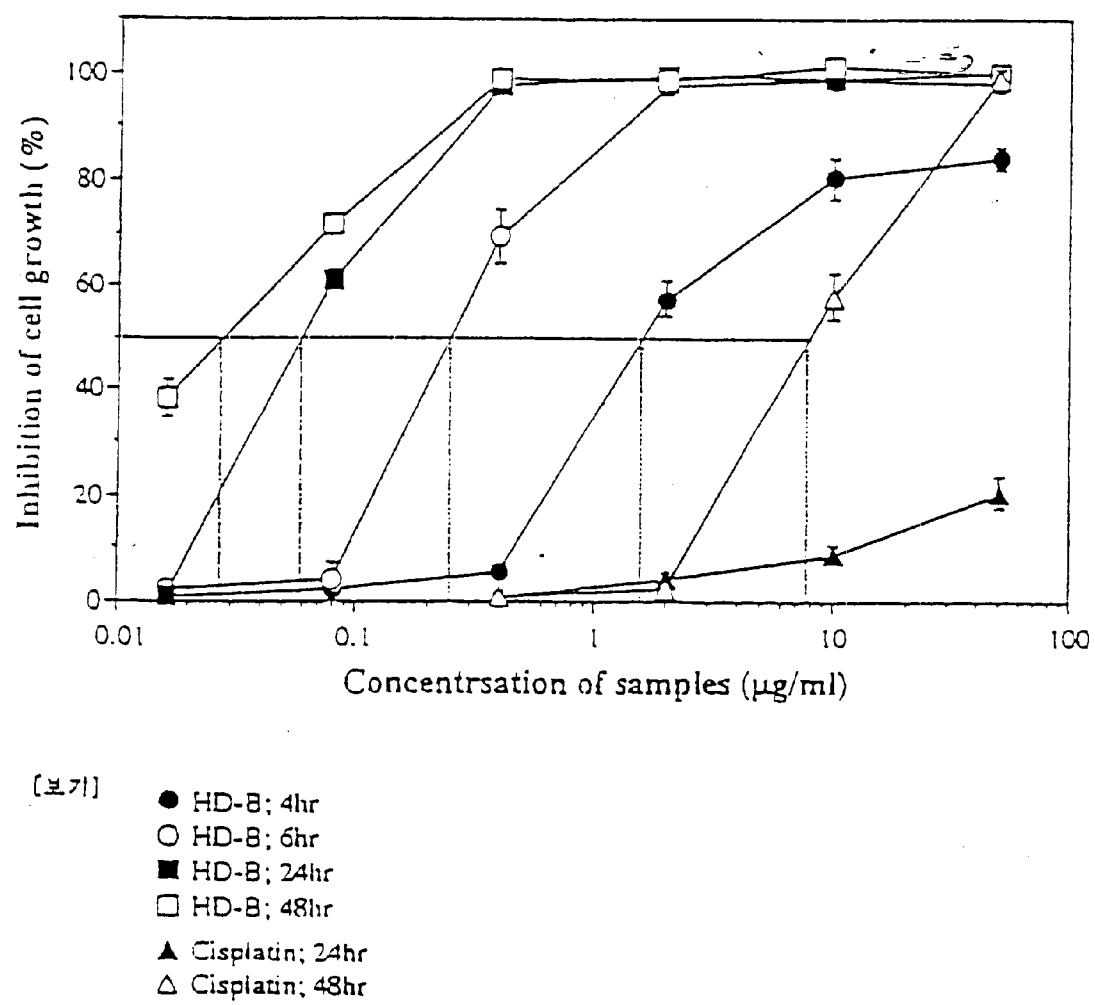
FIG. 3 shows the time course of anti-cancer efficacy of Sinsuk (arsenic hexoxide, $As_4O_6$) in vitro.

For further study of the cytotoxicity of each substance on cloned tumor cells, 3T3-fibroblast cells were cultured in test wells as described in experiment 1. After plating 3T3-fibroblast cells into test wells at a density of $1\times10^4/100$ μl, various concentrations of HD-2 and cisplatin were added to examine the time-courses (2, 4, and 6 hours after the addition) of cytotoxicity, which were measured by XTT method. As shown in FIG. 3, cisplatin did not show any cytotoxic effect up to 24 hours after the addition, but HD-2 demonstrated cytotoxic effect starting from 4 hours after the addition. $ED_{50}$s of HD-2 were 1.10 μg/ml and 0.21 μg/ml at 4 and 6 hours after the addition, respectively, which suggest that HD-2 showed an inhibitory effect on tumor growth from the begining of the phase. At the stage of 34 hours of treatment, the effect was also observed in morphological terms. In cisplatin group, partial necrosis of tumor cells or slowing of tumor growth was observed at this time. In contrast, complete necrosis of tumor cells was observed in HD-2 group to cause obvious changes in tumor morphology (such as breakdown of cell walls), which result in the loss of adhesiveness of cancer cells. This indicates that the direct killing effect of HD-2 is manifested within a short period of administration, compared with the effect of conventional chemotherapeutic agents, such as cisplatin. $ED_{50}$ HD-2 after 34 hours of administration was 60 ng/ml, but $ED_{50}$ of cisplatin could not be determined, although partial inhibition of tumor growth was observed after 24 hours of administration. At the end of the experiment (48 hours after administration), $ED_{50}$s were 30 ng/ml and 8 μg/ml for HD-2 and cisplatin, respectively. Thus cytotoxicity of HD-2 is about 270 times as high as that of cisplatin.

EXAMPLE 4

Mechanism of Cytotoxic Effect of HD-2

Cytotoxcity of HD-2 was further investigated to examine whether this effect was related to tumor cell death by apoptosis mechanism.

Figure 4:
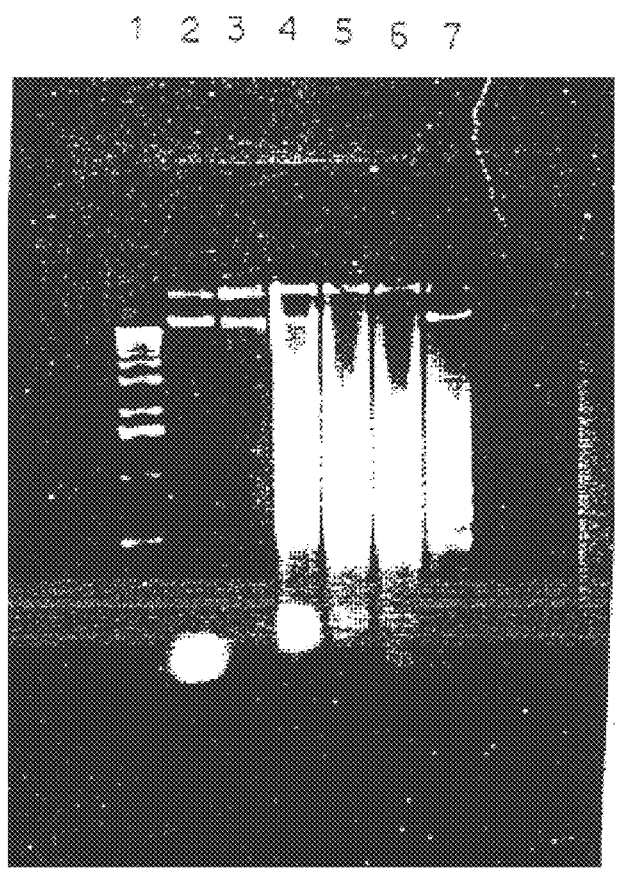
FIG. 4 shows the result of agarose-gel electrophoresis indicating that the anti-cancer effect of a natural chemical substance, $As_4O_6$, is due to apoptosis effect.

HL-60 cells were seeded at a density of $2\times10^4$ cells/ml and adequate concentration of HD-2 was dissolved in culture media, after which cisplatin was added to positive control group and culture media without cisplatin was added to negative control group. Cells were centrifuged after 24-hour incubation and precipitated cells were washed with physiological buffer solution (PBS) and incubated again in a buffer solution (500 mM Tris-Cl (pH 9.0), 20 mM EDTA, 10 mM NaCl, 1% SDS, and 500 mg/ml proteinase K) at 50° C. for 24 hours. Total DNA was collected using phenol extraction of cell lysate obtained by this treatment and was loaded on agarose gel plate for electrophoresis. As shown in FIG. 4, DNA segmentation at ~180 bp, which is a typical finding of apoptosis, was observed at 2.5 to 25 μg/ml concentrations of HD-2.

EXAMPLE 5

Acute Toxicity of HD-2

The acute toxicity of oral administration of HD-2 was evaluated according to toxicity assessment criteria described in Article 96-8 of Notice on Food and Drug Safety (Apr. 16, 1994). Rats (Sprague Dawley strain) were used for animal experiments. Dosage of a single, oral administration ranged from 0.4 to 1.25 g/kg body weight in male rats and 0.4 to 0.625 kg/kg body weight in female rats. General conditions of the animals, toxic symptoms, and mortality were measured every hour for the initial 6 hours following the single administration and once a day afterwards for 14 days. Body weights were measured before starting the study, 7 days after the administration, and at autopsy. Expired rats were studied to find the cause of death at autopsy. At the end of the study, all living rats were killed by an overdose of ether anesthesia and major organs were examined for pathological findings with the naked eyes. With maximal dose in male rats (1.25 g/kg body weight), mortality reached 100% during the study period. With high dose in male rats (0.85 g/kg body weight), mortality was 60% and with medium dose (0.8 g/kg body weight), mortality was 10%. In female rats, mortality was 100% with maximum-dose group (0.625 g/kg body weight), 80% in high-dose group (0.62 g/kg body weight), and 40% in medium-dose group (0.58 g/kg body weight). Clinical symptoms within 3 days of oral administration ranged from dose-dependent depression and dyspnea. Some rats manifesting these clinical symptoms expired, but others recovered to normal condition within 2 to 3 days of clinical symptoms. Changes in weight did not show any significant difference between the study and the control groups in all subgroups of different dosages. Autopsy of rats expired during the study period revealed findings of expanded stomach and engorged liver. Significant findings related to HD-2 administration were not observed in autopsy of killed rats at the end of the study.

With oral administration of HD-2 in Sprague-Dawley rats, $LD_{50}$ (50% Lethal Dose) was 0.81 g/kg body weight in male rats and 0.58 g/kg body weight in female rats. The results are summarized in Table 6.

TABLE 6

Mortality of male and female Sprague-Dawley rats following oral administration of HD-2

| sex | Dose (g/kg B. W.) | Hours after treatment 1 | 2 | 3 | 4 | 5 | 6 | Days after treament 1 | 2 | 3 | 4 | 5 | 6 | 7 | 8 | 9 | 10 | 11 | 12 | 13 | 14 | Final mortality |
|---|---|---|---|---|---|---|---|---|---|---|---|---|---|---|---|---|---|---|---|---|---|---|
| male | 1.25 | 0 | 0 | 0 | 0 | 0 | 0 | 3 | 1 | 0 | 0 | 0 | 0 | 0 | 0 | 0 | 0 | 0 | 0 | 0 | 0 | 5/5 (100%) |
|  | 0.85 | 0 | 0 | 0 | 0 | 0 | 0 | 2 | 1 | 0 | 0 | 0 | 0 | 0 | 0 | 0 | 0 | 0 | 0 | 0 | 0 | 3/5 (60%) |
|  | 0.8 | 0 | 0 | 0 | 0 | 0 | 0 | 1 | 1 | 0 | 0 | 0 | 0 | 0 | 0 | 0 | 0 | 0 | 0 | 0 | 0 | 2/5 (10%) |
|  | 0.6 | 0 | 0 | 0 | 0 | 0 | 0 | 0 | 0 | 0 | 0 | 0 | 0 | 0 | 0 | 0 | 0 | 0 | 0 | 0 | 0 | 0/5 (0%) |
|  | 0.4 | 0 | 0 | 0 | 0 | 0 | 0 | 0 | 0 | 0 | 0 | 0 | 0 | 0 | 0 | 0 | 0 | 0 | 0 | 0 | 0 | 0/5 (0%) |
|  | 0 | 0 | 0 | 0 | 0 | 0 | 0 | 0 | 0 | 0 | 0 | 0 | 0 | 0 | 0 | 0 | 0 | 0 | 0 | 0 | 0 | 0/5 (0%) |
| Female | 0.625 | 0 | 0 | 0 | 0 | 0 | 0 | 1 | 0 | 0 | 0 | 0 | 0 | 0 | 0 | 0 | 0 | 0 | 0 | 0 | 0 | 5/5 (100%) |
|  | 0.62 | 0 | 0 | 0 | 0 | 0 | 0 | 3 | 1 | 0 | 0 | 0 | 0 | 0 | 0 | 0 | 0 | 0 | 0 | 0 | 0 | 4/5 (80%) |
|  | 0.58 | 0 | 0 | 0 | 0 | 0 | 0 | 1 | 1 | 0 | 0 | 0 | 0 | 0 | 0 | 0 | 0 | 0 | 0 | 0 | 0 | 2/5 (40%) |
|  | 0.5 | 0 | 0 | 0 | 0 | 0 | 0 | 0 | 0 | 0 | 0 | 0 | 0 | 0 | 0 | 0 | 0 | 0 | 0 | 0 | 0 | 0/5 (0%) |
|  | 0.4 | 0 | 0 | 0 | 0 | 0 | 0 | 0 | 0 | 0 | 0 | 0 | 0 | 0 | 0 | 0 | 0 | 0 | 0 | 0 | 0 | 0/5 (0%) |
|  | 0 | 0 | 0 | 0 | 0 | 0 | 0 | 0 | 0 | 0 | 0 | 0 | 0 | 0 | 0 | 0 | 0 | 0 | 0 | 0 | 0 | 0/5 (0%) |

EXAMPLE 6

Subacute Toxicity of HD-2

The subacute toxicity of oral administration of HD-2 was evaluated according to toxicity assessment criteria described in Article 96-8 of Notice on rood and Drug Safety (Apr. 16, 1994). Rats (Sprague Dawley strain) were used for experiments, as was the case for acute toxicity experiments. Dosage of oral administrations was 100 (high dose), 10 (medium dose), and 1 mg (low dose) per kg body weight, which were administered once a day for 4 weeks (total 28 administrations).

Following items were observed during the period of study.
1) General symptoms: General symptoms, such as anorchism, salivation, diarrhea, vomiting, polyuria, anuria, and fecal change and the severity of these symptoms were evaluated once a day during the study period.
2) Food consumption: Twice a week, the amount of consumed food and the remaining amount were checked per cage.
3) Water consumption: Twice a week, the amount of consumed water and the remaining amount were checked per cage.
4) Weight: Weights were measured twice a week until the end of the study.
5) Urinalysis: Urine samples were collected during study period from 5 randomly selected rats per study subgroup and appearance, volume, and colors were recorded. Using urinalysis kits (N-multistix of Amersham), pH, gravity, leukocyte, protein, ketone body, urobilinogen, glucose and blood urea nitrogen were measured.
6) Eye examination: Ophthalmoscopic examination of 5 randomly selected rats per study subgroup was performed to evaluate the external appearance, cornea, and fundus of the eye.
7) Hematological and biochemical analysis: Routine blood test was done to measure red blood cell count, white blood cell count, hemoglobin concentration, number of monocytes and lymphocytes, and blood coagulation time. Biochemical analysis of serum was done to measure the activity of albumin transferase, aspartate transaminase, alkaline phosphate, and albumin.
8) Size and weight of organs: For every animal studied, weight and size of major organs were measured relative to body weight. Measured organs included liver, kidney, spleen, heart, adrenal gland, brain, thyroid gland, ovary, and testis.
9) Pathological examination: Organs were fixed in formalin after measurement of weight and size and fixed tissues were cut into 5-mm slices using microtome (AO Rotate Microtome) and stained with hematoxylin and eosin for microscopic study.

During the study, fatal cases were not observed and no specific clinical symptom, including changes in weight and consumption of food and water, was observed. Also any significant abnormality was not observed on urinalysis and eye examination. Hematological and biochemical study did not reveal any significant difference between the study and the control groups. On Pathological examination at autopsy, hemosiderin located in the cytoplasm of proximal tubular epithelium and atrophy of proximal tubular epithelium of kidney were observed to a slight degree in high-dose group (100 mg/kg body weight), but not in medium-dose, low-dose, and control groups. Other than this, no pathological finding to have dose-dependent property or to be related to HD-2 administration was observed. These results are summarized in Table 7. Therefore, oral administration of HD-2 lasting for 4 weeks did not cause any significant hematological abnormality in high-dose group (100 mg/kg body weight), but mild pathological finding suggestive of a slight renal abnormality was observed. However in medium-dose group, no such pathology was observed.

TABLE 7

Biochemical parameters of female rats treated with oral dose of HD-2

| /Group Parameter/Dose(g/kg/day) /No. of animal | Control 0 10 | Low 0.03 10 | Medium 0.3 10 | High 3.0 10 |
|---|---|---|---|---|
| ALT ($\mu$/l) | 37.66$^a$ ± 7.91 | 27.10 ± 11.63 | 27.00 ± 9.42 | 29.67 ± 10.55 |
| AST ($\mu$/l) | 118.53 ± 20.23 | 70.10* ± 30.11 | 87.53 ± 11.89 | 77.87* ± 23.89 |
| ALP ($\mu$/dl) | 67.00 ± 52.37 | 24.00 ± 7.00 | 38.00 ± 8.76 | 34.00 ± 14.73 |
| CREAT (mg/dl) | 0.37 ± 0.15 | 0.40 ± 0.17 | 0.53 ± 0.15 | 0.47 ± 0.15 |
| BUN (mg/dl) | 13.00 ± 2.26 | 11.43 ± 4.28 | 13.18 ± 3.62 | 13.13 ± 4.60 |
| ALB (g/dl) | 3.27 ± 1.27 | 3.60 ± 1.54 | 3.70 ± 1.16 | 3.33 ± 0.99 |
| GLU (mg/dl) | 50.33 ± 30.86 | 67.70 ± 46.60 | 70.00 ± 32.04 | 63.03 ± 40.83 |
| TB | 0.19 ± | 0.14 ± | 0.16 ± | 0.18 ± |

TABLE 7-continued

Biochemical parameters of female rats treated with oral dose of HD-2

| /Group Parameter/Dose(g/kg/day) /No. of animal | Control 0 10 | Low 0.03 10 | Medium 0.3 10 | High 3.0 10 |
|---|---|---|---|---|
| (mg/dl) | 0.07 | 0.05 | 0.07 | 0.01 |
| Ca (mg/dl) | 8.30 ± 3.03 | 8.77 ± 3.18 | 8.95 ± 2.64 | 8.73 ± 3.25 |
| CL (meq/dl) | 90.00 ± 26.00 | 87.33 ± 28.01 | 91.00 ± 23.47 | 88.33 ± 26.31 |
| TP (g/dl) | 5.87 ± 2.05 | 6.27 ± 2.24 | 6.53 ± 1.89 | 5.93 ± 2.11 |
| CHOL (mg/dl) | 40.33 ± 17.79 | 42.33 ± 21.01 | 40.50 ± 11.36 | 44.33 ± 13.01 |
| TG (mg/dl) | 46.00 ± 27.06 | 50.00 ± 17.35 | 56.25 ± 29.49 | 62.33 ± 20.53 |

[a]indicates mean ± SD,
*significant difference compared with control group ($P < 0.05$) ALT:alanine transferase, AST:aspartate transferase, CHOL:cholesterol, GLU:glucose, TB:total bilirubin, TP:total protein, TG:tirglyceride, ALP:alkaline phosphate, Ca:calcium, CL:chloride CREAT:creatine, BUN:blood urea nitrogen, ALB:albumin

EXAMPLE 7

Effect of HD-2 on Cancer Metastasis

EXPERIMENT 1

Inhibitory Effect of Orally-administered HD-2 on Cancer Metastasis

Utilizing mouse model, the inhibitory effect of HD-2 on cancer metastasis was evaluated with cloned tumor cells and compared with cisplatin. As single administration of 500 mg/kg body weight per day did not have any side effect in rats (see EXAMPLE 5), inhibitory effect of HD-2 on cancer metastasis was studied employing dose below 500 mg/kg body weight. B16-BL6 melanoma cells or colon26-M3.1 carcinoma cells were inoculated into mice and number of metastatic tumor masses appearing in lungs was counted. After the inoculation of tumor cells, various doses of HD-2 Or cisplatin were administered one day after the inoculation to find the optimum concentration for anti-metastatic efficacy. Seven days after the inoculation, HD-2 Or cisplatin was administered to measure therapeutic efficacy on grown tumor mass. As shown in Table 8, Oral administration of HD-2 (0.1 to 10 mg) had significant anti-metastatic effect compared to the control group (cisplatin group). The peak activity was observed at 1-mg dose with very high anticancer efficacy (86%). A, 7th day when inoculated tumor cells settled completely in target organs, oral administration of HD-2 demonstrated anti-metastatic efficacy of 70%. This indicated oral administration of HD-2 was quite effective for treatment of established cancer.

TABLE 8

Inhibitory effect of orally-administered HD-2 on cancer metastasis

| Concentration, administration route & day | number of metastatic masses (inhibitory rate(%)) | |
|---|---|---|
| | mean ± SD | range |
| Experiment I. Control group (injection of B16-BL6) | 122 ± 20 | 101–146 |

TABLE 8-continued

Inhibitory effect of orally-administered HD-2 on cancer metastasis

| Concentration, administration route & day | number of metastatic masses (inhibitory rate(%)) | |
|---|---|---|
| | mean ± SD | range |
| HD-2 | | |
| 10 mg oral administration + 1 | 45 ± 25(63.1) | 72–23 |
| 1 mg oral administration + 1 | 17 ± 9*86.1) | 8–29 |
| 0.1 mg oral administration + 1 | 75 ± 28(38.5) | 105–51 |
| Experiment II. Control group (injection of B16-BL6) HD-2 | 162 ± 24 | 133–188 |
| 10 mg oral administration + 7 | 55 ± 13(66.1) | 40–67 |
| 1 mg oral administration + 7 | 48 ± 19(70.4) | 26–69 |
| 0.1 mg oral administration + 7 | 95 ± 23(41.4) | 118–72 |

EXPERIMENT 2:

Inhibitory Effect of Intravenously-administered HD-2 on Cancer Metastasis

Similar to Experiment 1, the inhibitory effect of HD-2 on cancer metastasis was compared with cisplatin, using cloned tumor cells possessing high metastatic capability. In this experiment, HD-2 was administered intravenously with dosage less than 500 mg/kg body weight per day. As summarized in Table 9, 10- to 100-$\mu$g HD-2 had anti-metastatic efficacy above 90%, which suggested that HD-2 was more effective that cisplatin at the same dose. Ten micrograms of HD-2 and cisplan, which is considered as a optimum dose to inhibit cancer metastasis at 7th day of tumor cell innoculation, had anticancer effect of 67.5% and 50.0%, respectively, when administered intravenously. This suggests that the anticancer efficacy of HD-2 is better than the conventional anticancer drugs and HD-2 is also effective in treating full-grown cancer at terminal stage.

TABLE 9

Inhibitory effect of intravenously-administered HD-2 on cancer metastasis

| Concentration, administration route and day | number of metastatic mass (inhibitory rate(%)) | |
|---|---|---|
| | mean ± SD | range |
| Experiment I. | | |
| Control group (injection of colon tumor cells) HD-2 | 155 ± 26 | 122–179 |
| 100 $\mu$g intravenous administration + 1 | 15 ± 15(90.3) | 2–28 |
| 10 $\mu$g intravenous administration + 1 | 11 ± 19(92.9) | 1–29 |
| 1 $\mu$g intravenous administration + 1 | 52 ± 28(66.5) | 27–71 |
| cisplatin | | |
| 100 $\mu$g intravenous administration + 1 | 57 ± 22(63.2) | 32–80 |
| 10 $\mu$g intravenous administration + 1 | 20 ± 13(87.1) | 8–32 |
| 1 $\mu$g intravenous administration + 1 | 102 ± 28(34.2) | 84–127 |
| Experiment II. | | |
| Control group (injection of colon tumor cells) | 154 ± 14 | 142–167 |

TABLE 9-continued

Inhibitory effect of intravenously-administered HD-2 on cancer metastasis

| Concentration, administration route and day | number of metastatic mass (inhibitory rate(%)) | |
|---|---|---|
| | mean ± SD | range |
| HD-2 | | |
| 10 μg intravenous administration + 7 cisplatin | 50 ± 11(67.5) | 39–65 |
| 10 μg intravenous administration + 7 | 77 ± 12(50.0) | 5–88 |

EXAMPLE 8

Anticancer Mechanism of HD-2 in vivo

Figure 5:
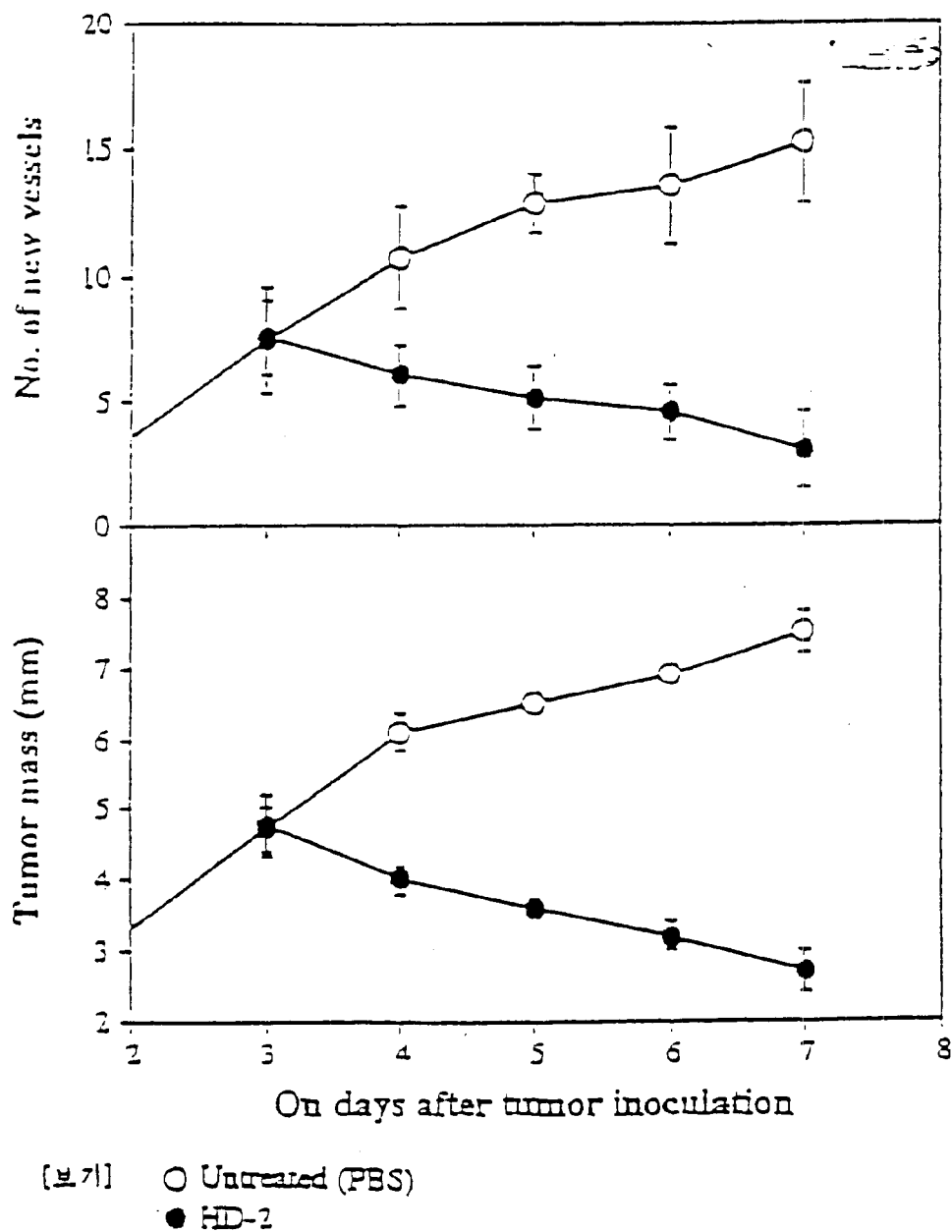
FIG. 5 shows the inhibitory effect of $As_4O_6$ on neovascularization in tumor mass.

The in vivo mechanism of anticancer effect of HD-2 was studied in mice. After suspending $4 \times 10^5$ cells of B16-BL6 melanoma in 50% PBS, they were injected intradermally into 2 sites on the back of 6- to 7-week old C57BL/6 mice. Three days after the tumor injection, one milligram of HD-2 was given orally and size of inoculated melanoma and number of blood vessels at and around tumor sites were measured. Control group was treated with oral administration of PBS. As demonstrated in FIG. 5, number of new blood vessels, which are observed in cancer proliferation and metastasis, tended to decrease following the administration of HD-2. Also the size of solid tumor mass decreased significantly in proportion to decrease in the number of new blood vessels. It is suggested that HD-2 suppresses the invasion into and the adhesion onto tissues, which goes hand in hand with the formation of new blood vessels.

EXAMPLE 9

Inhibitory Effect of HD-2 on Carcinogen-induced Oncogenesis

Figure 6:
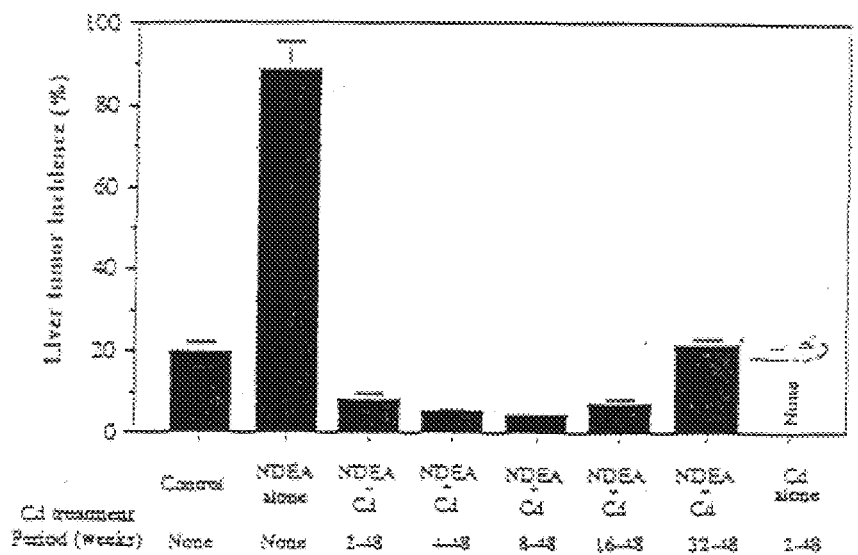
FIG. 6 shows that $As_4O_6$ decreases hepatoma incidence induced by a carcinogen (NDEA).
Figure 7:
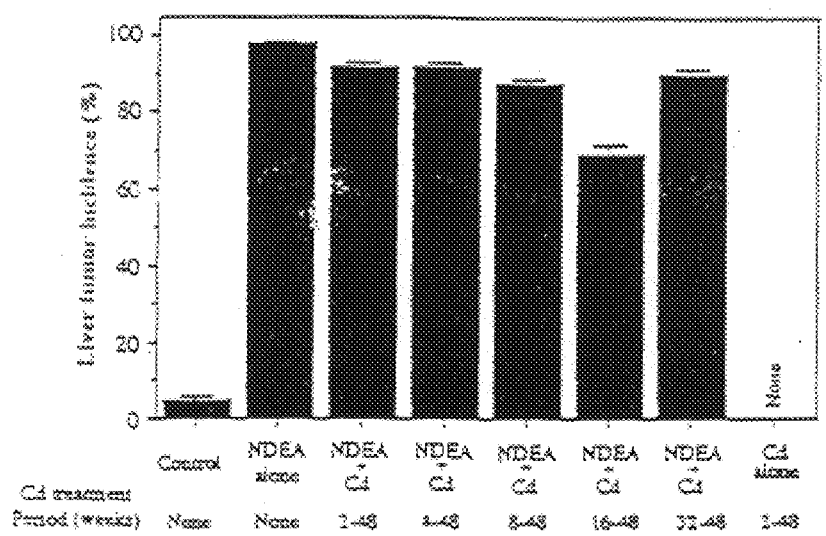
FIG. 7 shows that $As_4O_6$ decreases the incidence of lung cancer induced by a carcinogen (NDEA).
Figure 8:
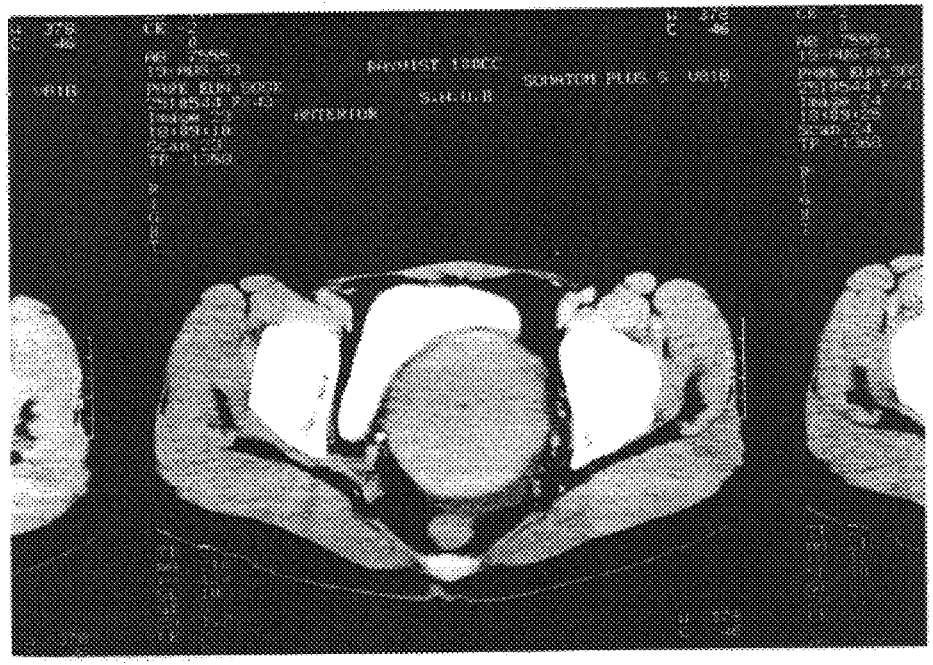
FIG. 8 is a CT (Computed Tomography) scan showing multiple tumor masses in uterus.
Figure 9:
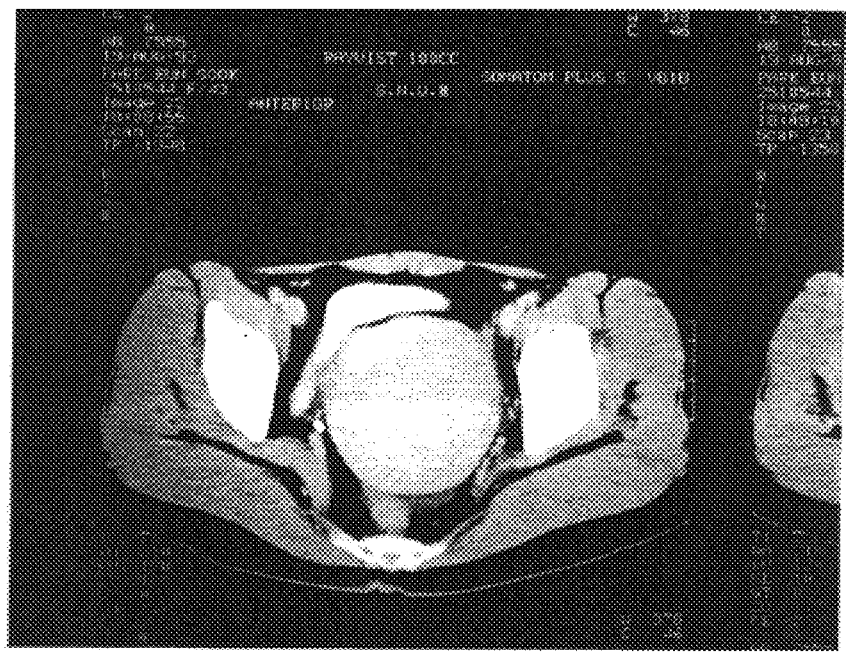
FIG. 9 is a similar CT scan as FIG. 8, indicating multiple tumor growth in uterus.
Figure 10:
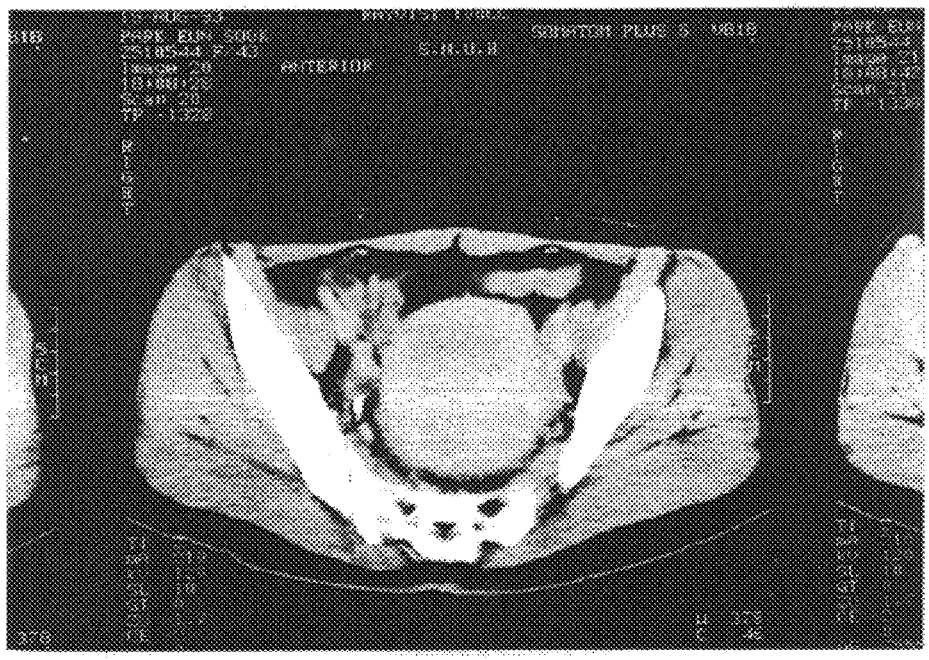
FIG. 10 is a CT scan of an enlarged uterus due to the invasion of tumor cells at the terminal stage of uterine carcinoma.
Figure 11:
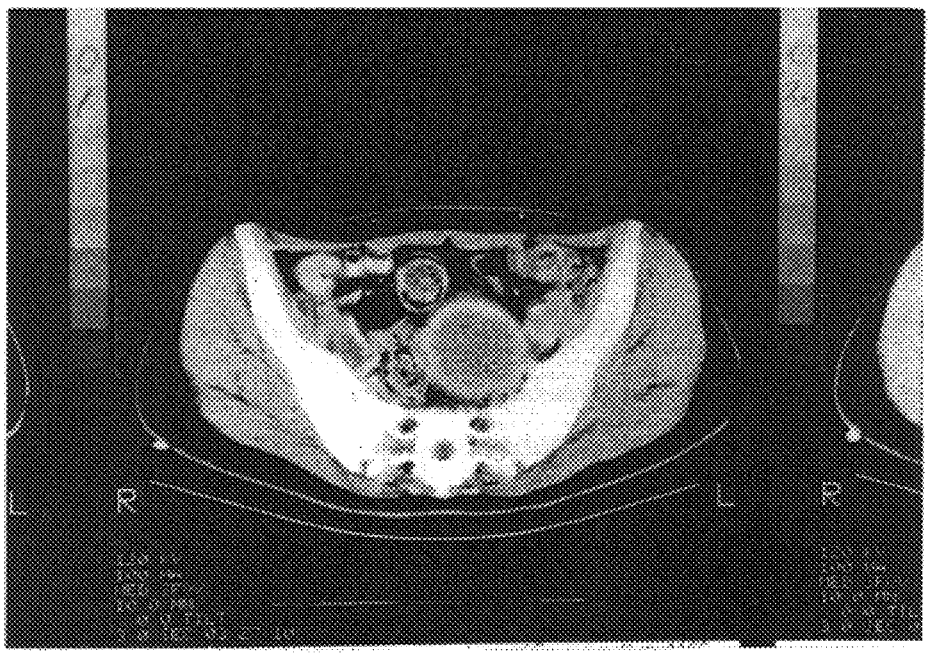
FIG. 11 is another CT scan of the same patient taken, at a different angle.
Figure 12:
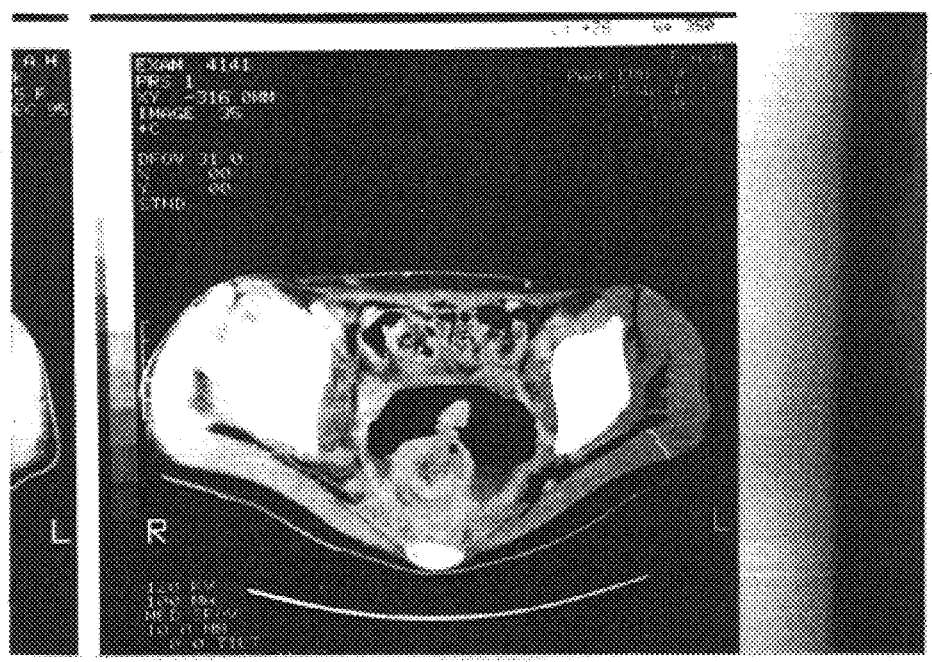
FIG. 12 is a CT scan of a uterus at terminal stage of uterine carcinoma, which shows several air shadows reflecting perforations on the uterine wall. This indicates disappearance of tumor mass following administration of $As_4O_6$.
Figure 13:
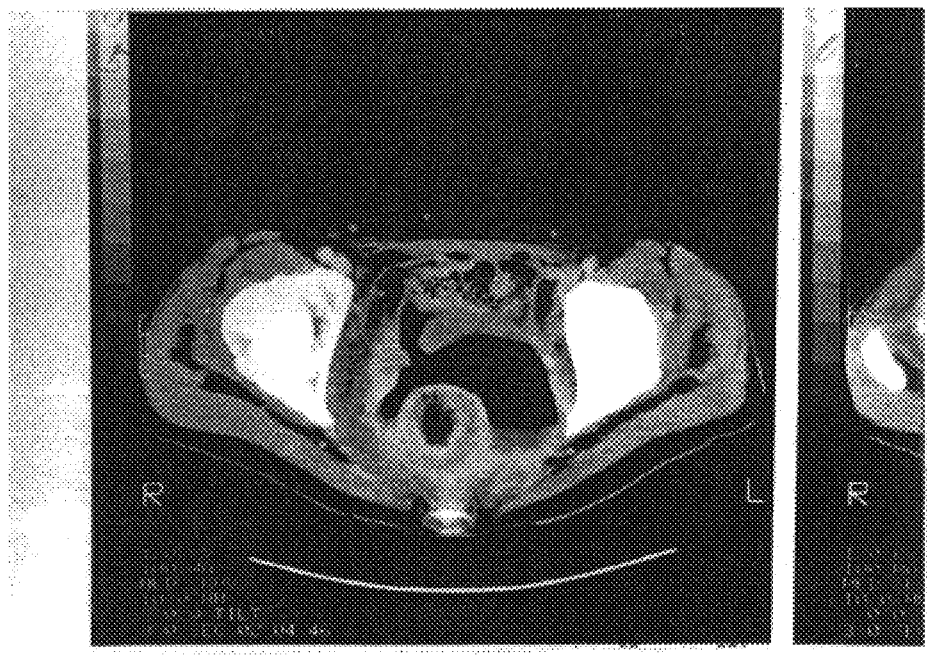
FIG. 13 is a CT scan of a patient with uterine carcinoma at terminal stage, which shows similar findings as in FIG. 12.
Figure 14:
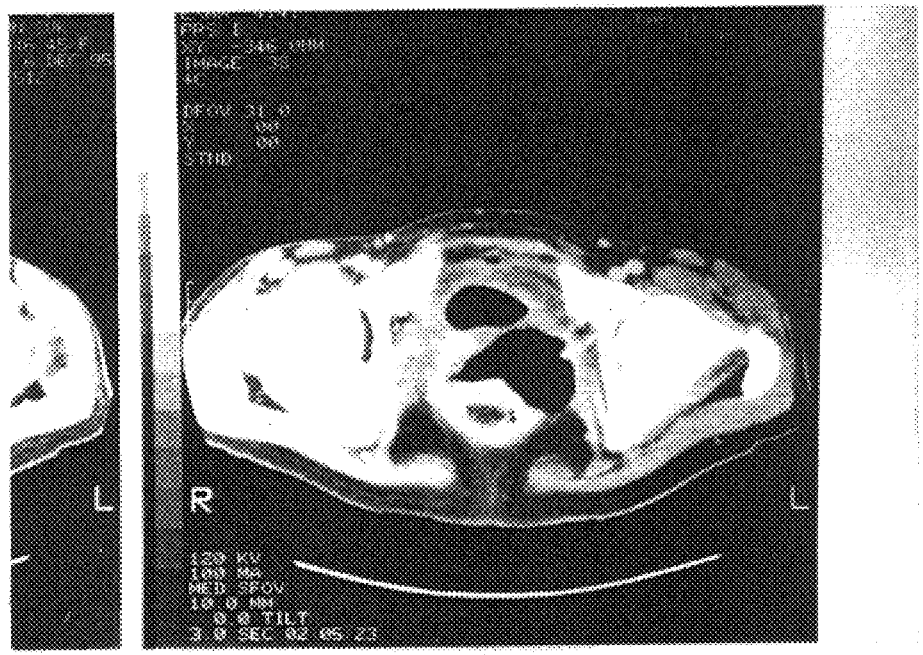
FIG. 14 is a CT scan of a patient with uterine carcinoma at terminal stage, which manifests similar findings as in FIG. 13.
Figure 15:
FIG. 15 is a CT scan of a patient with uterine carcinoma at terminal stage, which manifests similar findings as in FIG. 14.
Figure 16:
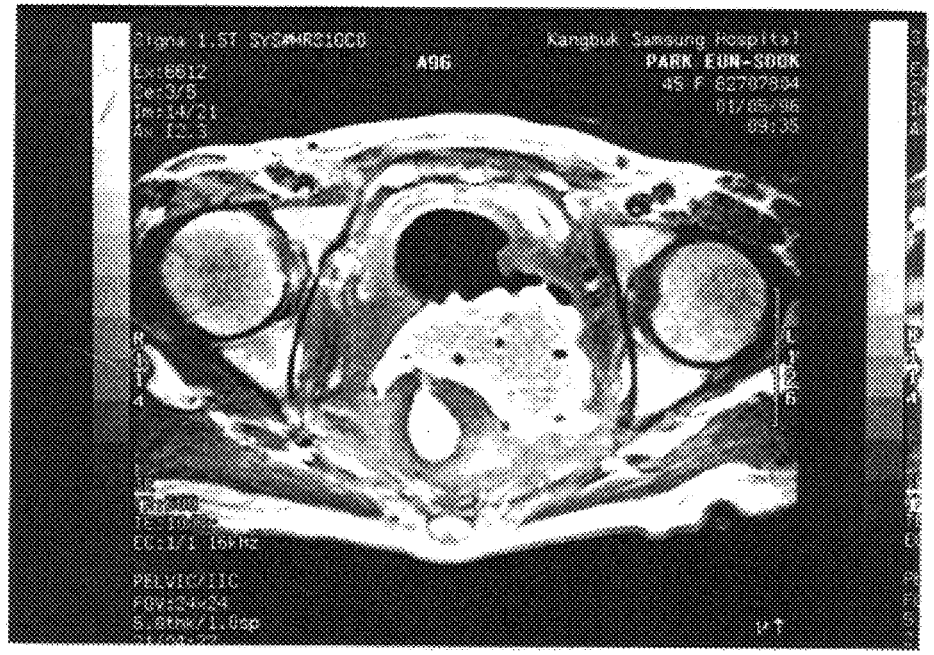
FIG. 16 is an MRI (Magnetic Resonance Imaging) scan of uterus filled with fecal material leaked from rectum through the opening of uterine perforation, which was formed after the disappearance of cancer mass.
Figure 17:
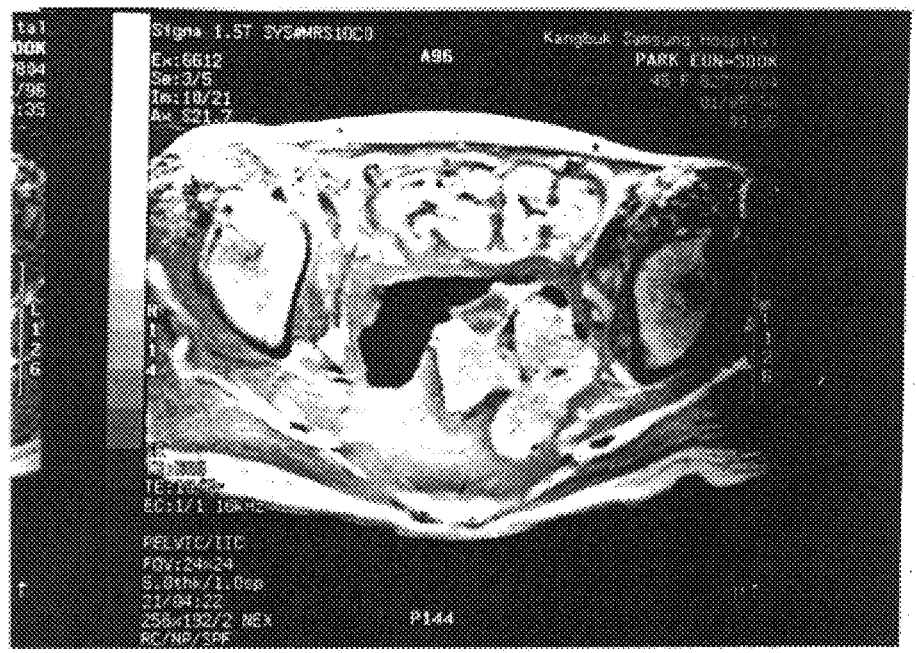
FIG. 17 is an MRI image manifesting similar findings as FIG. 16.
Figure 18:
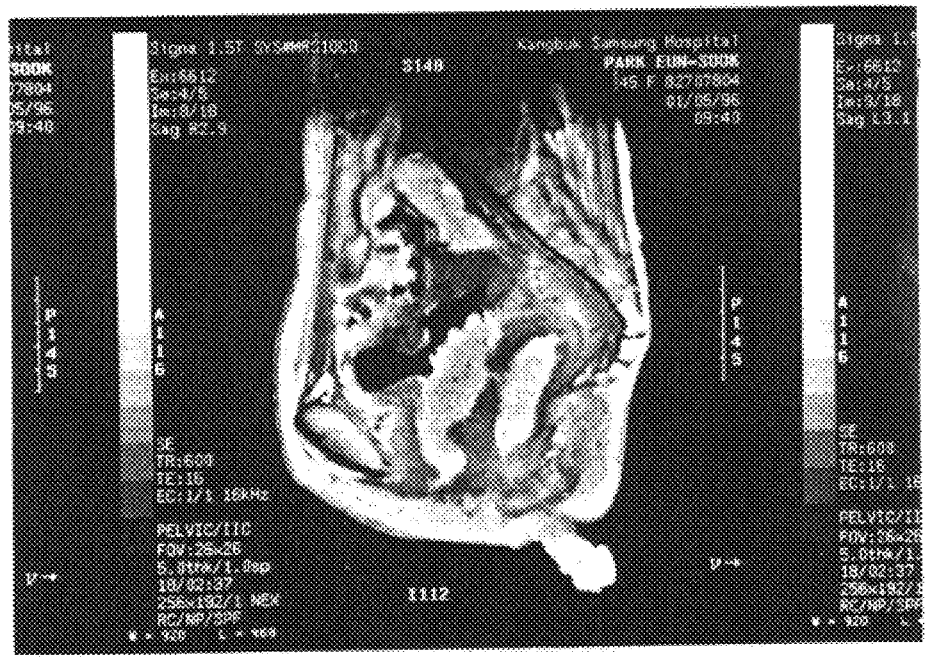
FIG. 18 is an MRI image of a uterus after the cure of tumor mass.
Figure 19:
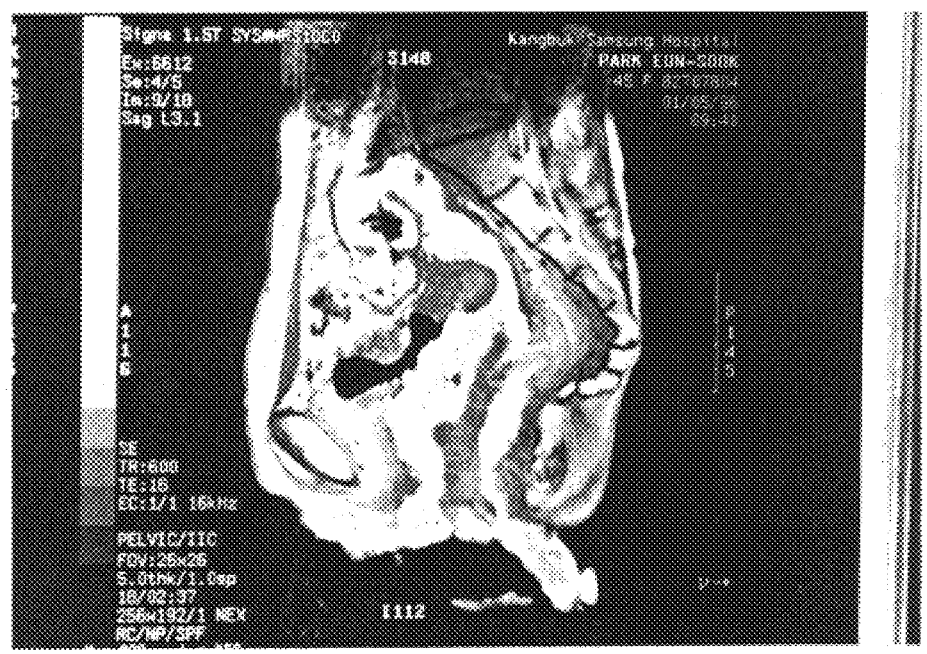
FIG. 19 is an MRI image of a patient with uterine carcinoma at terminal stage, which manifests similar findings as in FIG. 18.
Figure 20:
FIG. 20 is an MRI image of a patient with lung cancer at terminal stage, showing pleural fluids filling the right pleural cavity caused by right lung cancer.
Figure 21:
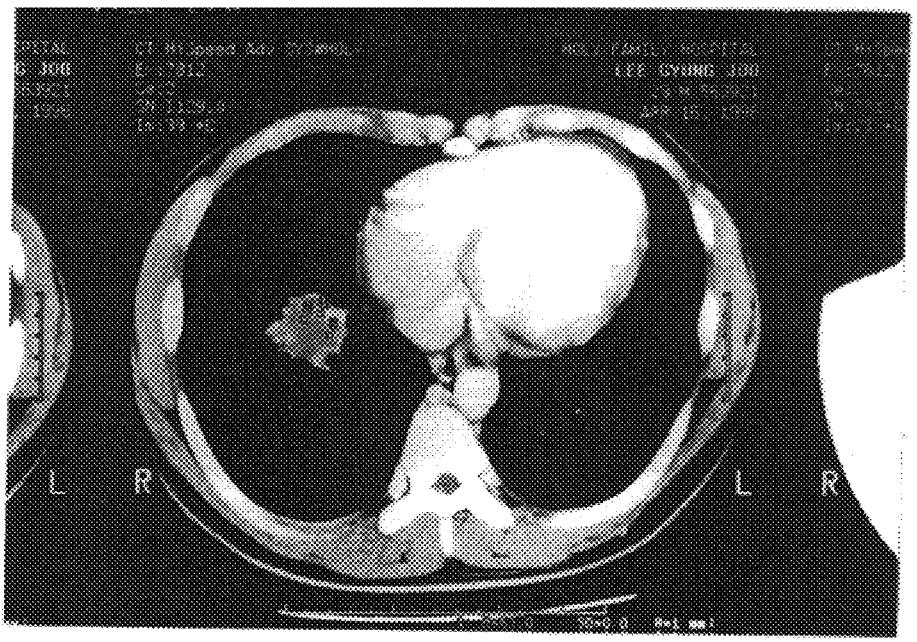
FIG. 21 is a CT scan of a patient with lung cancer at terminal stage, showing irregular tumor mass at right lung.
Figure 22:
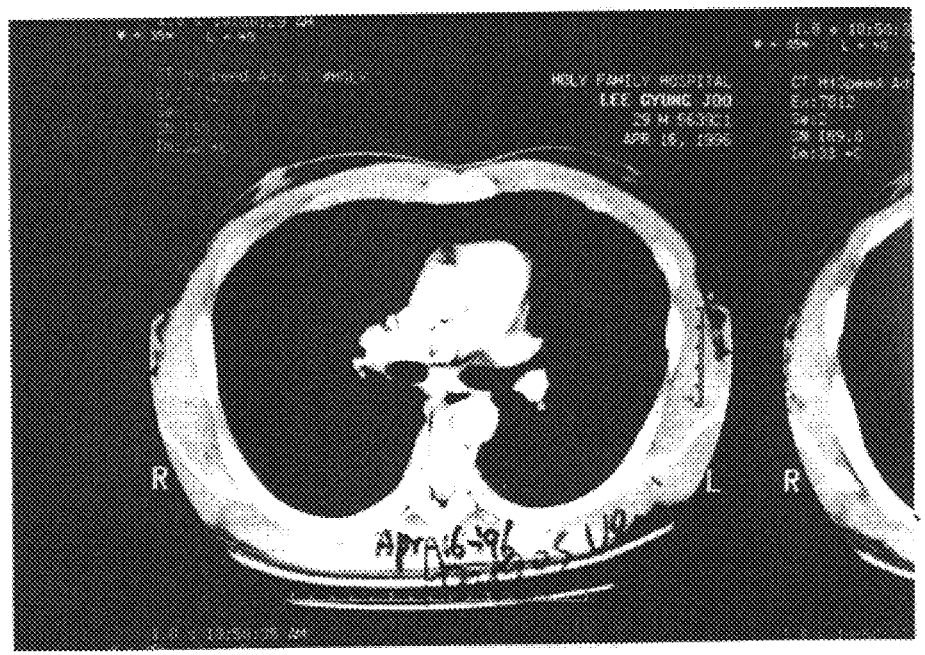
FIG. 22 is a CT scan of a patient with lung cancer at terminal stage, showing enlarged lymph nodes in mediastinum.
Figure 23:
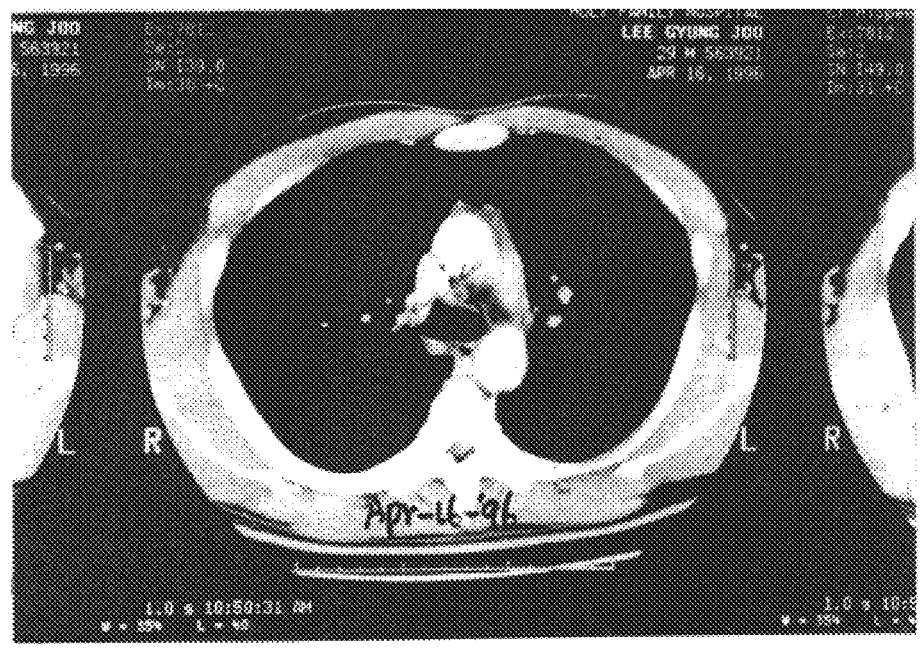
FIG. 23 is a CT scan of the same patient as in FIG. 22.
Figure 24:
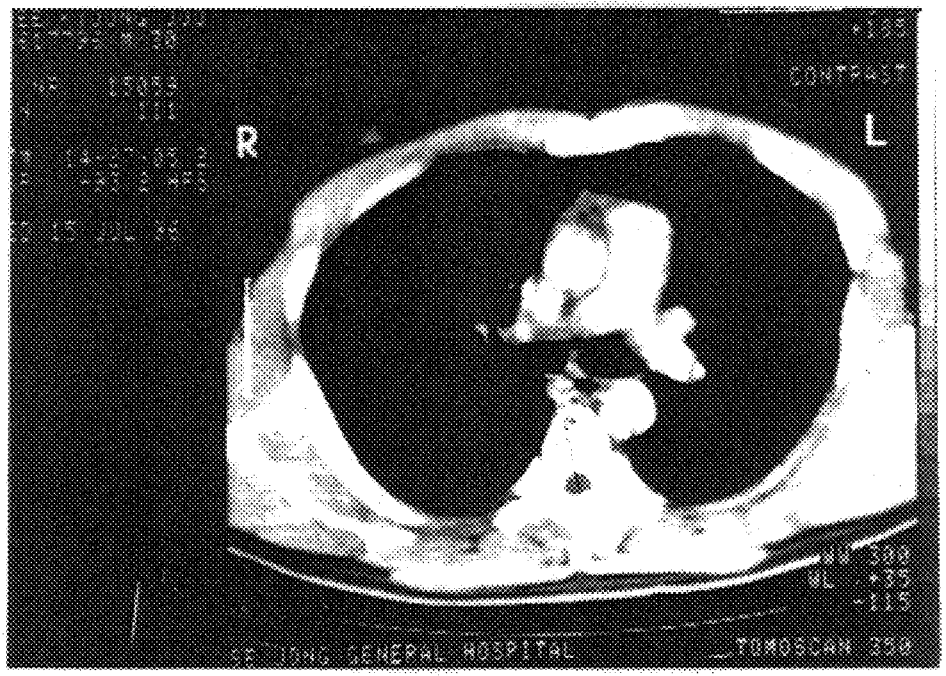
FIG. 24 is a CT scan of the same patient as in FIG. 23.
Figure 25:
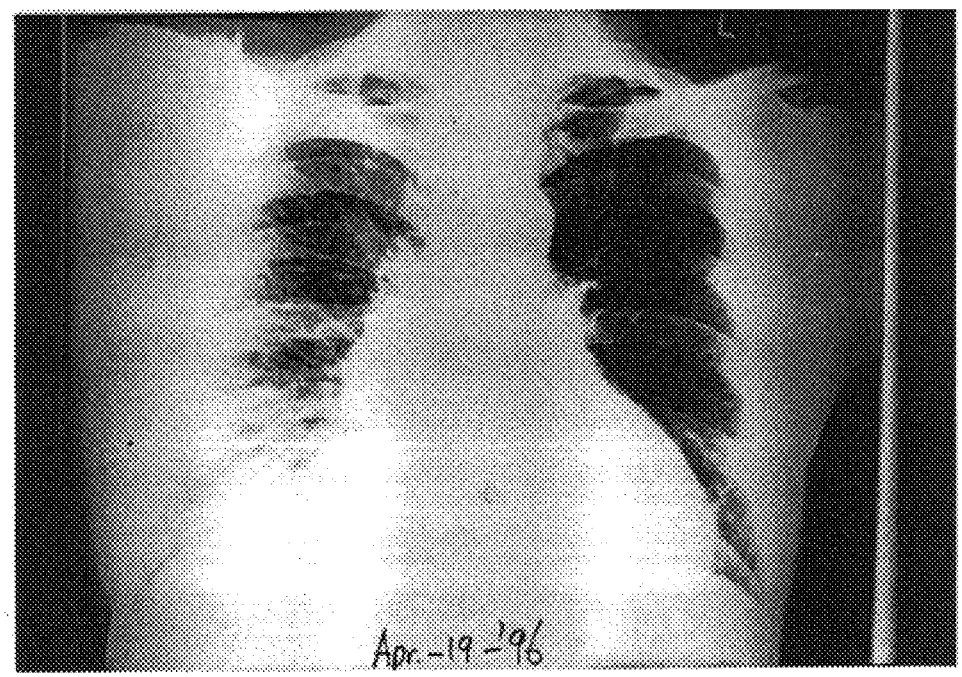
FIG. 25 is a CT scan of a patient with lung cancer at terminal stage, indicating that pleural fluid in right pleural cavity started to shrink in volume following the administration of pharmaceutical composition of $As_4O_6$.
Figure 26:
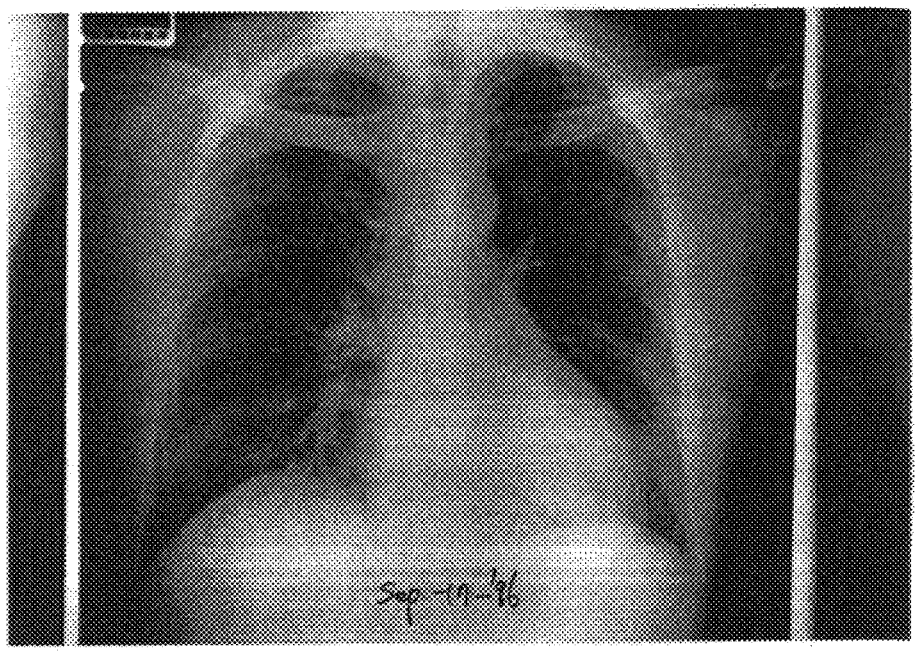
FIG. 26 is a CT scan of a patient with lung cancer at terminal stage, showing that pleural fluid in right pleural cavity was completely absorbed following the administration of pharmaceutical composition of $As_4O_6$.
Figure 27:
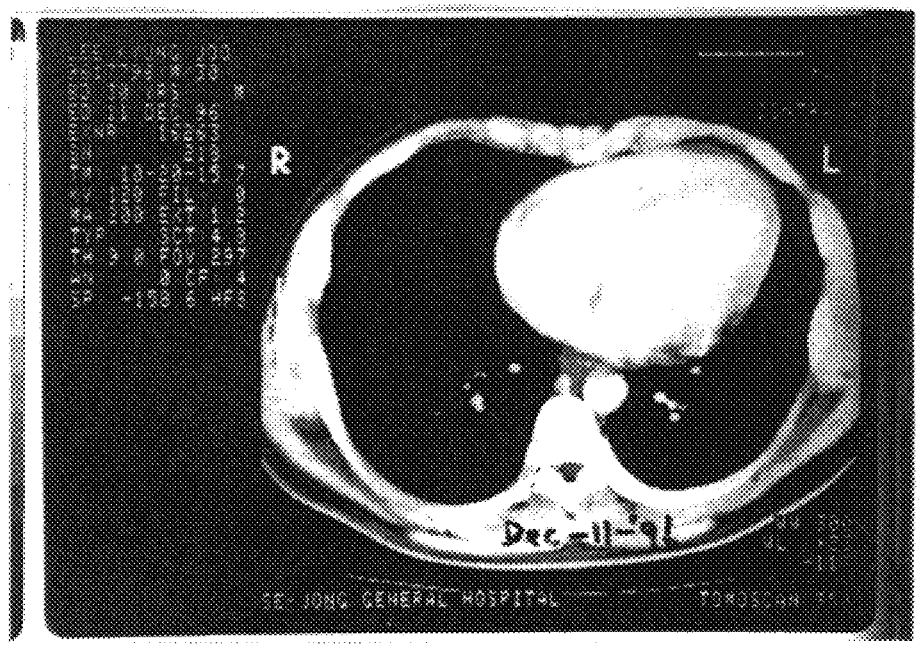
FIG. 27 is a CT scan of a patient with lung cancer at terminal stage, showing the shrinkage of lymph node to normal size following the administration of pharmaceutical composition of $As_4O_6$.
Figure 28:
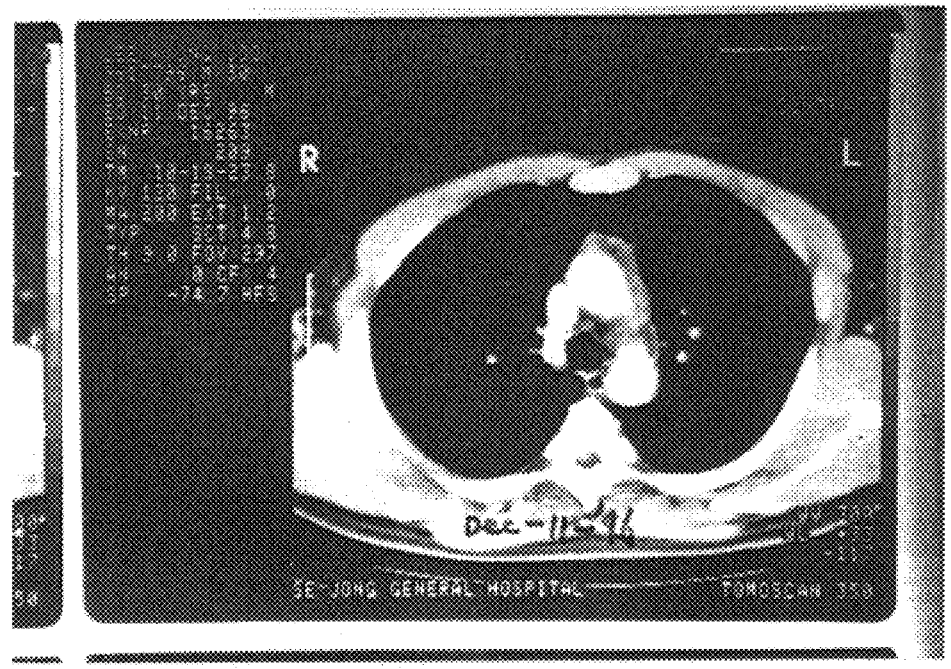
FIG. 28 is a CT scan manifesting the same findings as in FIG. 27.
Figure 29:
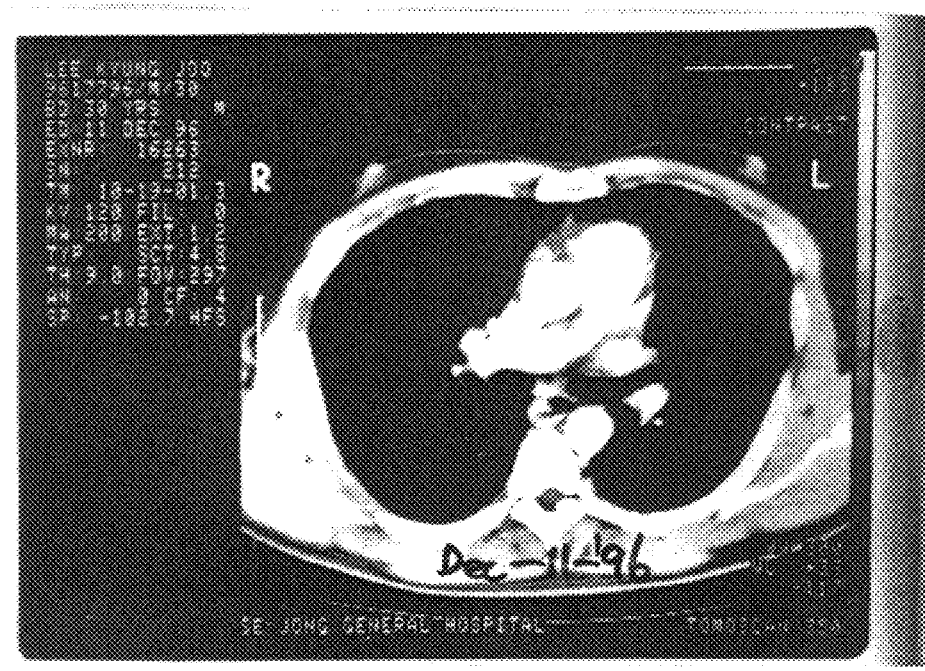
FIG. 29 is a CT scan manifesting the same findings as in FIG. 28.
Figure 30:
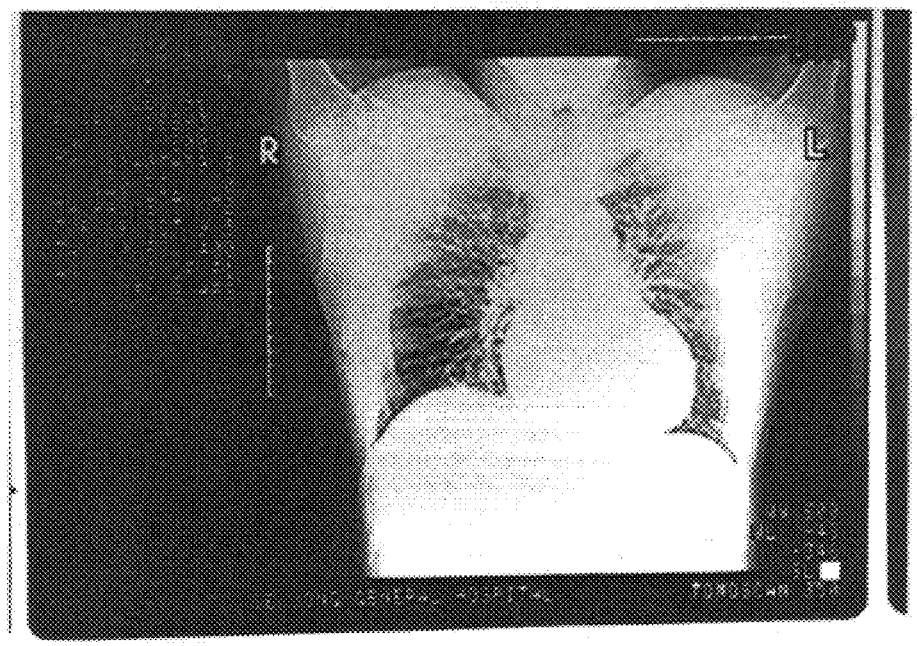
FIG. 30 is a CT scan manifesting the same findings as in FIG. 29.

To examine the inhibitory effect of HD-2 on carcinogen-induced oncogenesis, N-nitrosodiethylamine (NDEA) was injected as a carcinogen into peritoneal cavity of mouse (B6C3F1 strain) at a concentration of 90 mg per kg body weight to induce cancer. At 2, 4, 8, 16, and 32 weeks after carcinogen injection, 100 g of HD-2 was administered orally and the same amount of distilled water was injected into control group. Forty-two weeks after NDEA treatment, mice were sacrificed to measure the inicidence and the size of tumors formed in lung and liver. As shown in FIG. 6, the incidence of NDEA-induced hepatic tumor was effectively inhibited after oral administration of HD-2. The incidence of NDEA-induced hepatic tumor was above 90%, but following HD-2 administration, the incidence was lowered to 5 to 22%, despite of variation depending on the period of HD-2 administration. Thus HD-2 inhibited carcinogen-induced oncogenesis in liver by 78 to 95%. Also HD-2 inhibited spontaneous hepatoma completely, the incidence of which is reported about 20% without HD-2 administration. In lung, the inhibitory effect of HD-2 on reducing carcinogen-induced oncogenesis was not so dramatic as in liver. However, if HD-2 was given at 4 weeks after NDEA injection, carcinogen-induced oncogenesis was inhibited by 30%. Further, spontaneous cancers of lung were completely suppressed by HD-2, which indicates that oral administration of adequate dose of HD-2 decreases the incidence of spontaneous cancers. As shown in FIG. 7, the number of tumor masses in lung was about 2 in HD-2 group, compared to 7 in control group, which points to the efficacy of HD-2 in inhibition of carcinogen-induced oncogenesis. These results suggest that HD-2 was very effective not only in treatment but also in prevention of malignant cancers.

EXAMPLE 10

Preparation of Pharmaceutical Composition for Anticancer Therapy 5 g of HD-2 was mixed with the following ingredients of Chinese medicine and pulverized to a powder form: hodongjoo 7 g, chunsangap 7 g, baekchool 10 g, woowhang 3 g, sahyang 3 g, shingok 5 g, moryo 5 g, yongnyehyang 3 g, yoohyang, 5 g, molryak 5 g, baekbongryung 10 g, sangbaekpi 10 g, galgeun 10 g, macheehyun 5 g, ohmeeja 5 g, hyulgal 5 g, seokko 5 g, boongsa 5 g, hansooseok 5 g, and red steamed ginseng 7 g. Distilled water was added to the powder to form pills of 1 to 1.5 grams for oral administration. These pills were used to manufacture tablets of ~1.33 g convenient for a single dose, which were administered to cancer patients at terminal stage, three times a day to make a total of 4 grams per day. The effective dose of HD-2 may depend on the fraction of drugs and age, sex, and health conditions of the patient. In general, usual dosage was 50 g per kg body weight, with upper limit of 160 to 330 g per kg body weight. Although ingredients of Oriental medicine were utilized to prepare pharmaceutical composition for the clinical trial of HD-2, any pharmaceutical composition can be employed for this purpose. Chemically-synthesized arsenic hexoxide ($As_4O_6$) can be substituted for HD-2, which was prepared by separation and purification of Sinsuk in this study.

EXAMPLE 11

Clinical Trial on Various Forms of Malignant Cancers

Cancer patients diagnosed of cancer of uterus, lung, maxillary sinus, kidney, or urinary bladder at hospital by thorough clinical examinations were selected for the study and most were at the terminal stage of the disease with expected survival of 6 to 12 months. After acquiring consent from the patient or the guardian, tablets described in EXAMPLE 10 were administered 3 times a day to examine the anticancer efficacy.

EXPERIMENT 1

Clinical Trial on a Patient with Uterine Cancer

The study subject (EunSook Park) was diagnosed of cancer of uterine cervix (final diagnosis: squamous cell carcinoma) at Seoul National University Hospital on October 1993. Even after repeated anticancer therapy (8 times), cancer cells continued to grow and involve lymph nodes, rectum, and urinary bladder. Therefore urine was collected through a tube inserted into the right kidney and the patient was immobilized in bed and incapable of taking food. The doctor informed her of expected survival of less than 3 months. Tablets described in EXAMPLE 10 were administered to EunSook Park for 3 months and the progress was monitored using computed tomography (CT) and magnetic resonance imaging (MRI). CT scans (FIGS. 8 to 19) indicated that following the disappearance of tumor mass, perforations were formed in the walls of uterus, urinary bladder, a rectum and feces of rectum leaked into uterus through perforated openings, for which colostomy were done on the patient on January 1996.

EXPERIMENT 2

Clinical Trial on a Patient with Lung Cancer

The study subject (KyungJoo Lee) was a male of age 30 and treated for fever and chill with the diagnosis of pneumonia on Mar. 19, 1996 without any improvement of symptoms. He was diagnosed of stage-4 lung cancer (final diagnosis: undifferentiated adenocarcinoma) at SeongGa Hospital of Bucheon and confirmed of the diagnosis at Samsung Medical Center located at IlWonDong, Seoul with additional thorough examinations. The doctors told him of his limited lifetime of 6 to 12 months. CT scans (FIGS. 21 to 24), taken on Mar. 21, 1996 at SeongGa Hospital, showed irregular tumor mass at the right lung, pleural fluids filling the right pleural cavity, and enlarged lymph nodes in mediastinum. KyungJoo Lee was given the tablets prepared as described in EXAMPLE 10 for 8 months, while the progress of the disease was monitored using CT scanning. As indicated in FIGS. 25 to 30, tumor mass gradually shrank in size to disappear completely after 8 months of drug therapy.

EXPERIMENT 3

Clinical Trial on a Patient with Maxillary Sinus Cancer

Figure 31:
FIG. 31 is a CT scan of a cancer patient involving maxillary sinus at terminal stage, showing that right maxillary sinus was filled with tumor masses.
Figure 32:
FIG. 32 is a CT scan of the same patient as in FIG. 31, taken at a different angle.
Figure 33:
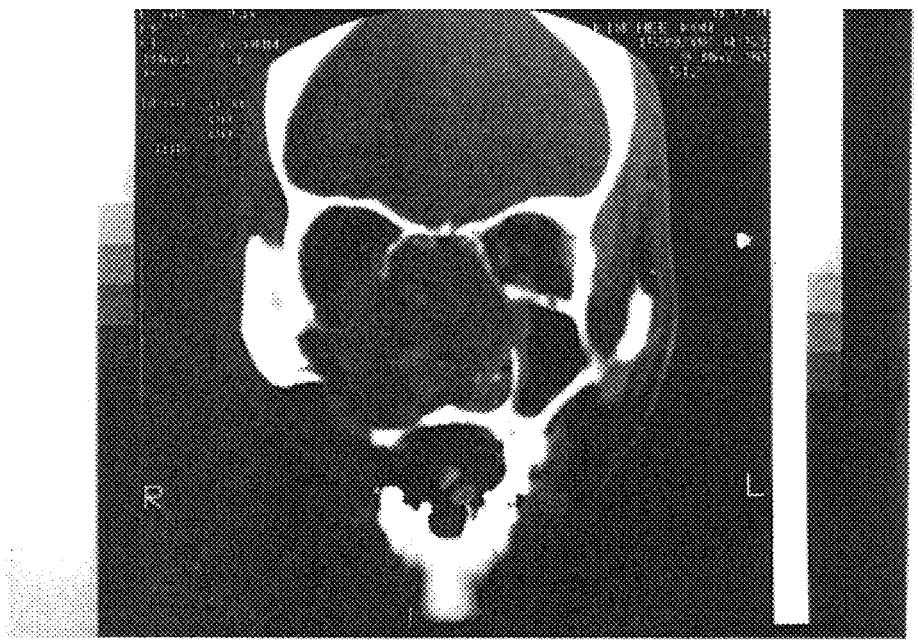
FIG. 33 is a CT scan of a patient with a cancer involving maxillary sinus, who was being treated for the cancer at a hospital.
Figure 34:
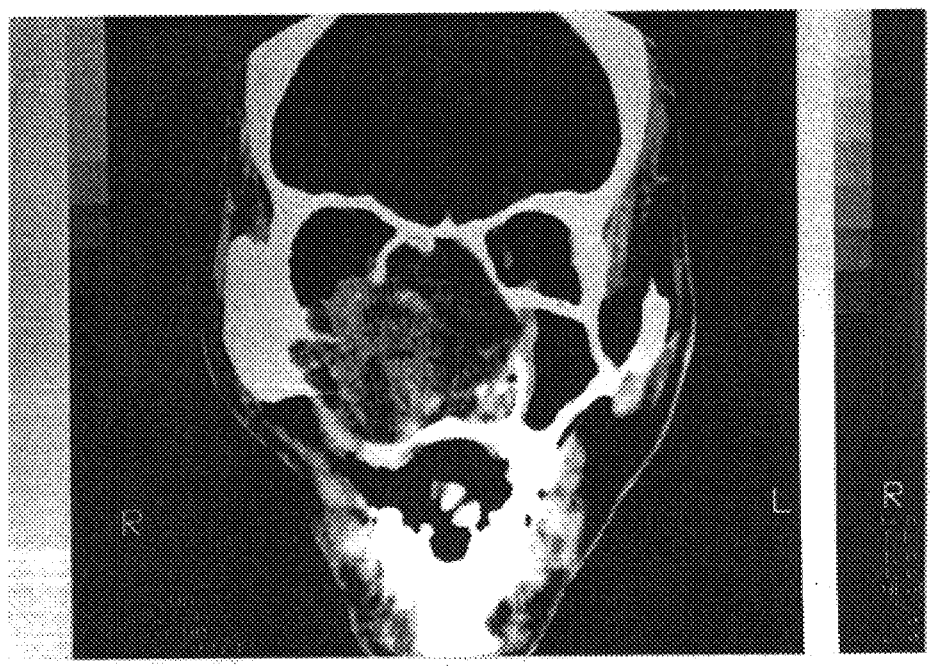
FIG. 34 is a CT scan of the same patient as in FIG. 33.
Figure 35:
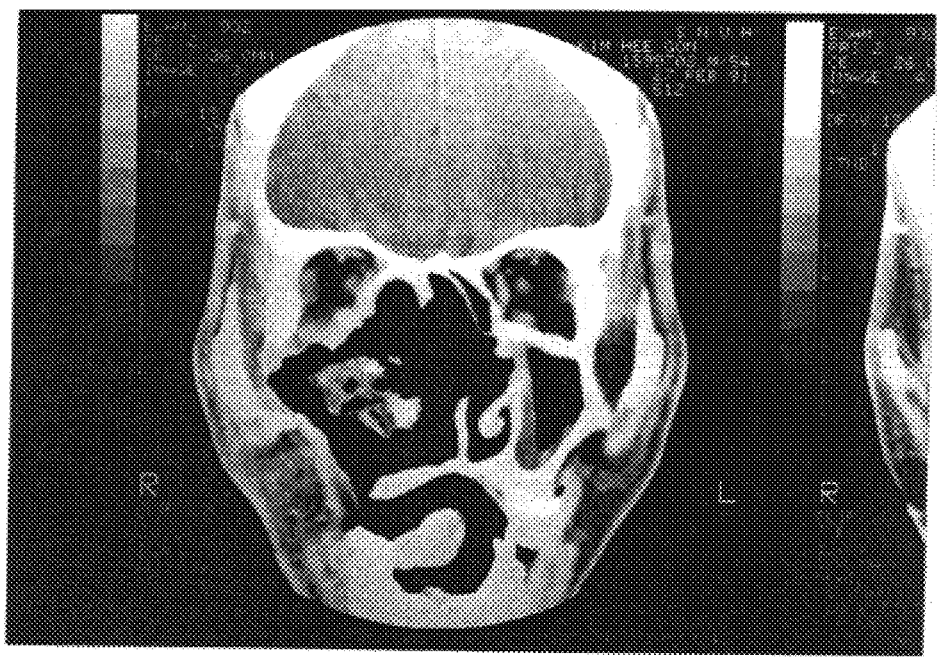
FIG. 35 is a CT scan of a patient with a cancer involving maxillary sinus at terminal stage, showing that cancerous masses in right nasal cavity and maxillary sinus were cured following the administration of pharmaceutical composition of $As_4O_6$.
Figure 36:
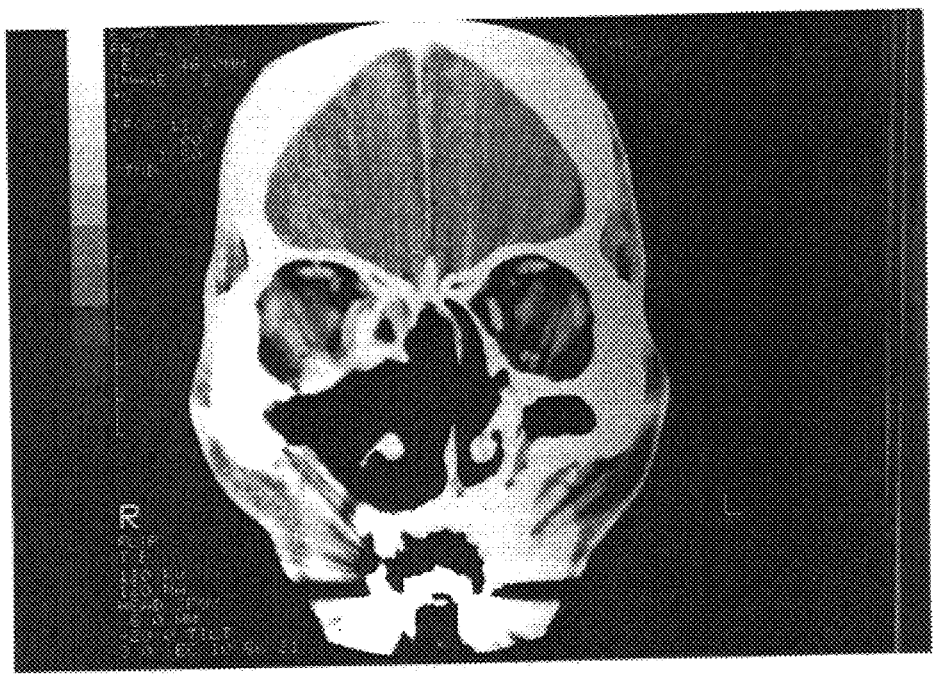
FIG. 36 is a CT scan manifesting the same findings as in FIG. 35.
Figure 37:
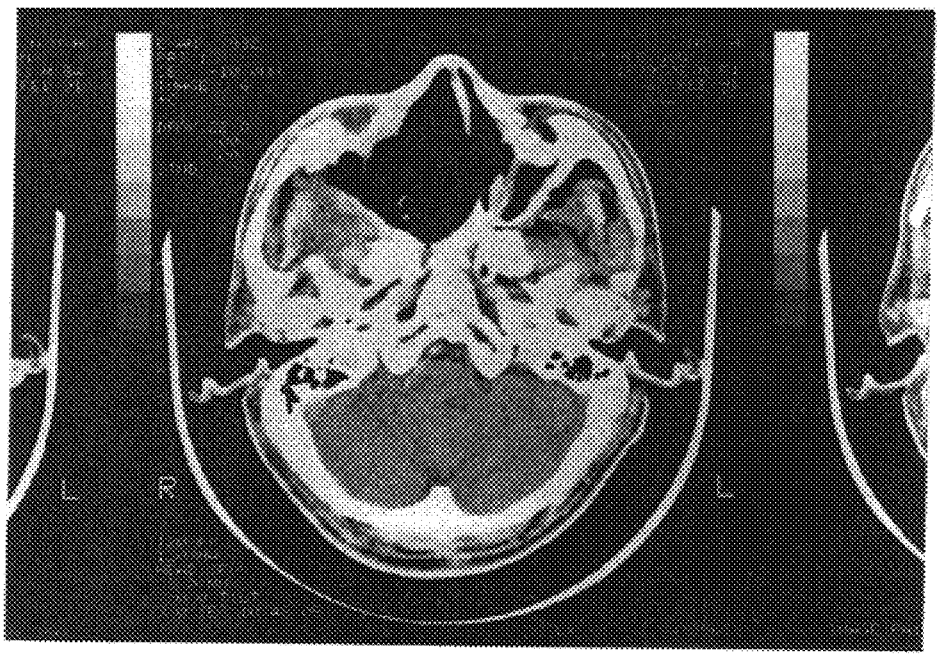
FIG. 37 is a CT scan manifesting the same findings as in FIG. 36.
Figure 38:
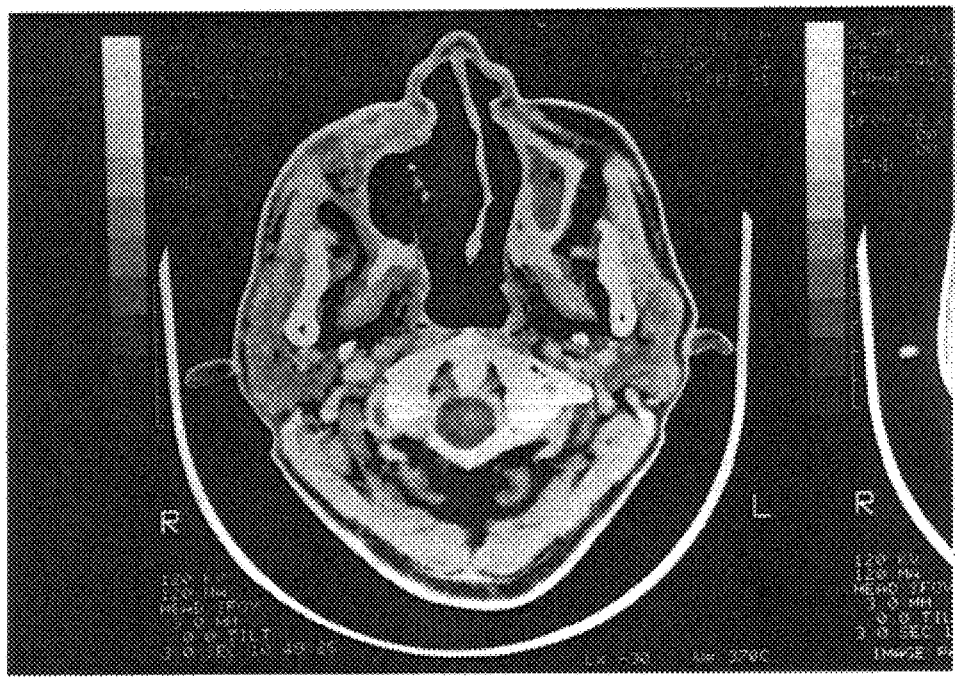
FIG. 38 is a CT scan manifesting the same findings as in FIG. 37.
Figure 39:
FIG. 39 is an IVP (IntraVenous Pyelogram) of a patient with kidney cancer at terminal stage, showing a tumor mass located at left renal pelvis.
Figure 40:
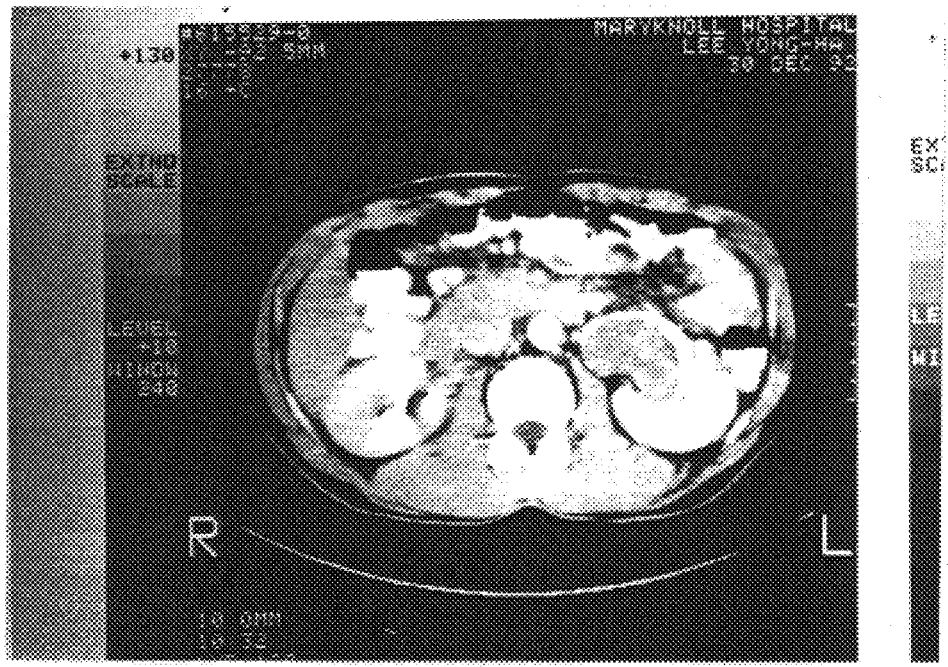
FIG. 40 is an IVP of the same patient as in FIG. 39.
Figure 41:
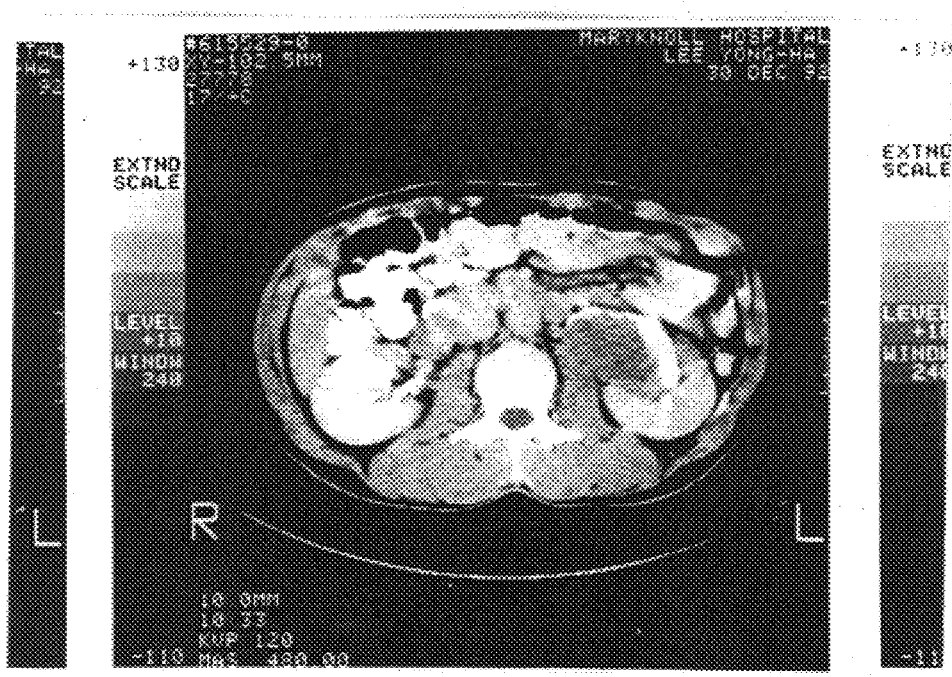
FIG. 41 is IVP of a patient with kidney cancer at terminal stage, showing a tumor mass located in left renal pelvis growing toward renal artery.
Figure 42:
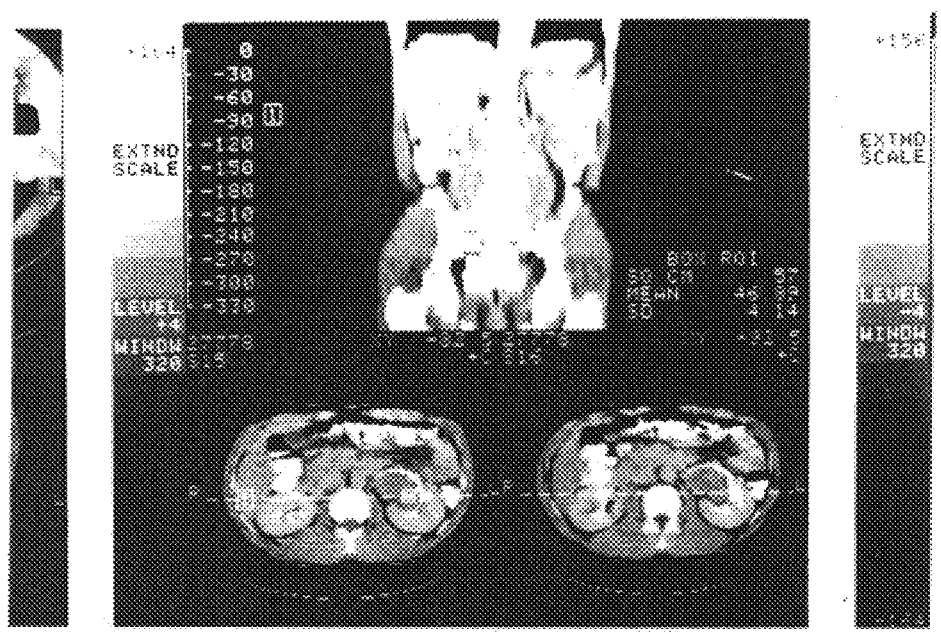
FIG. 42 are CT scans, taken at different angles, of both kidneys of a patient with kidney cancer at terminal stage.
Figure 43:
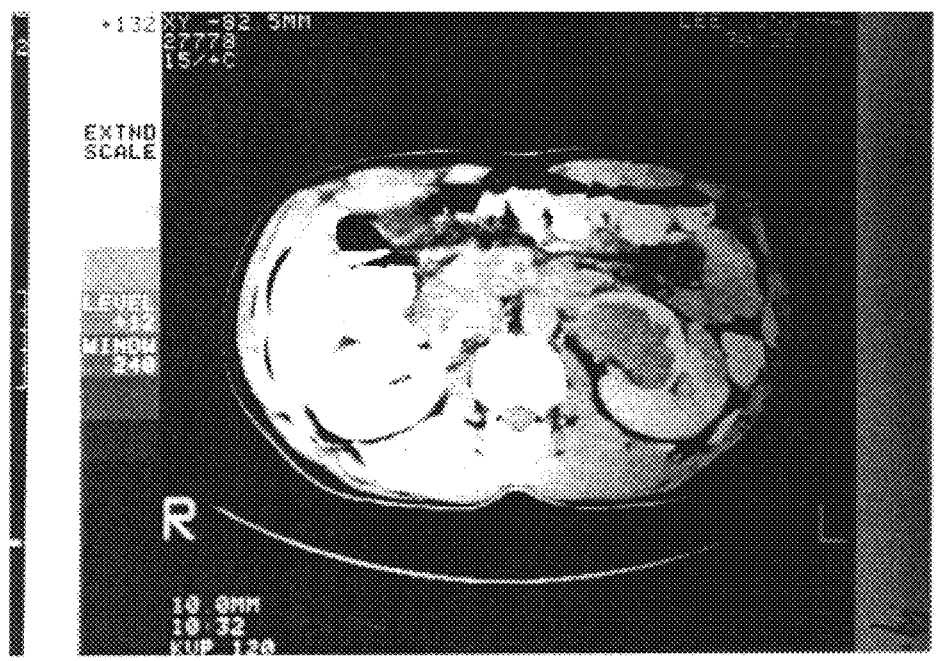
FIG. 43 are CT scans of a patient with renal carcinoma at terminal stage, demonstrating the same findings as in FIG. 42.
Figure 44:
FIG. 44 are CT scans of a patient with renal carcinoma at terminal stage, demonstrating the same findings as in FIG. 43.

The study subject (HeeGon Kim) was diagnosed of malignant cancer involving right nasal cavity and maxillary sinus (final diagnosis: adenoid cystadenoma) in 1981, which was inoperable due to metastasis to bone. He had been treated with chemotherapy and radiation therapy at CheonJu Jesuit Hospital and Seoul National University Hospital, but the disease became worse. He was advised to prepare for his death after a CT scan on Mar. 5, 1990. As shown in CT scans taken on Mar. 31, 1990 (FIGS. 31 and 32), right maxillary sinus was filled with tumor masses and tumor mass was also observed in right nasal cavity. Cancer specialists at Seoul National University Hospital prescribed anticancer chemotherapy for 2 months, but CT scans taken after completing the chemotherapy indicated additional growth of tumor masses to involve nearby brain regions, right eyeball, and right and left nasal cavity. HeeGon Kim was given the tablets prepared as described in EXAMPLE 10 for 3 months and the progress of the disease was checked using CT scanning on Feb. 27, 1991 at Seoul National University Hospital. CT scans (FIGS. 35 to 38) indicated that most of the tumor masses were gone and right nasal cavity and maxillary sinus were filled with normal flow of air.

EXPERIMENT 4

Clinical Trial on a Patient with Kidney Cancer

Figure 45:
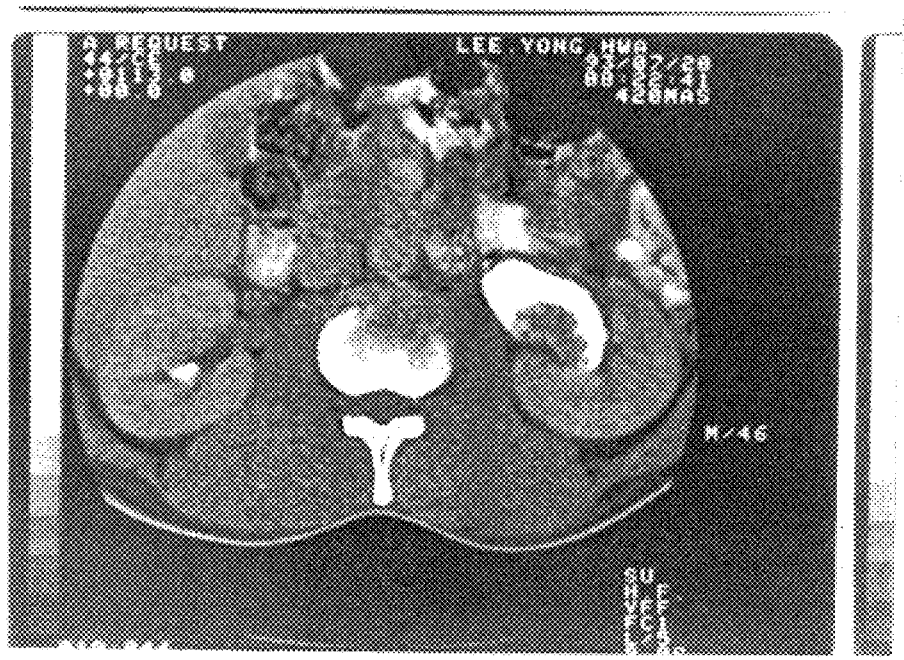
FIG. 45 is a CT scan of a patient with renal carcinoma at terminal stage, showing the shrinkage of a cancerous mass following the administration of pharmaceutical composition of $As_4O_6$.
Figure 46:
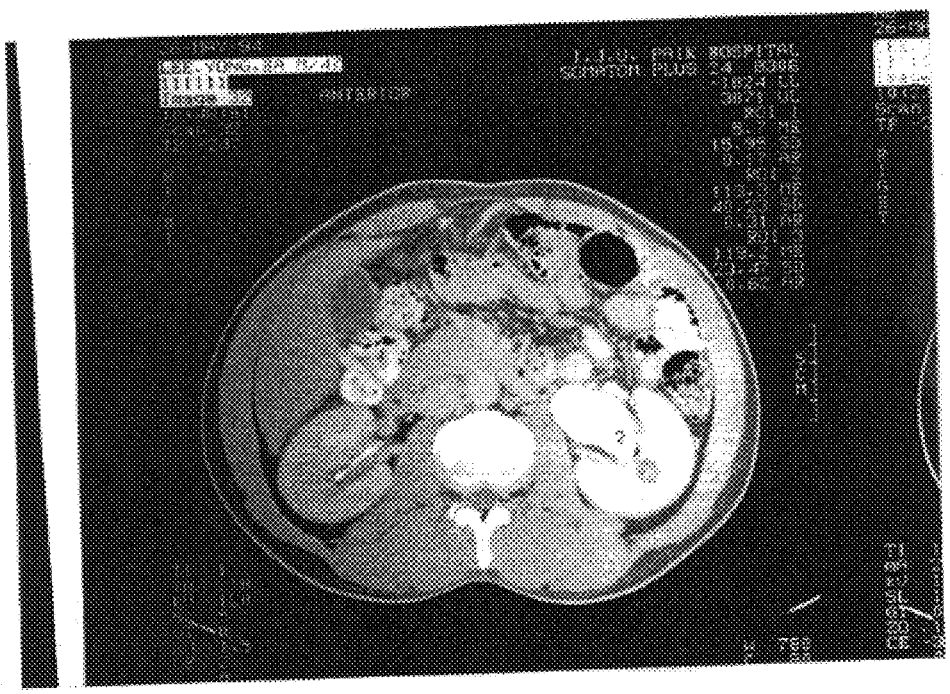
FIG. 46 is a CT scan of a patient with renal carcinoma at terminal stage, demonstrating the same findings as in FIG. 45.
Figure 47:
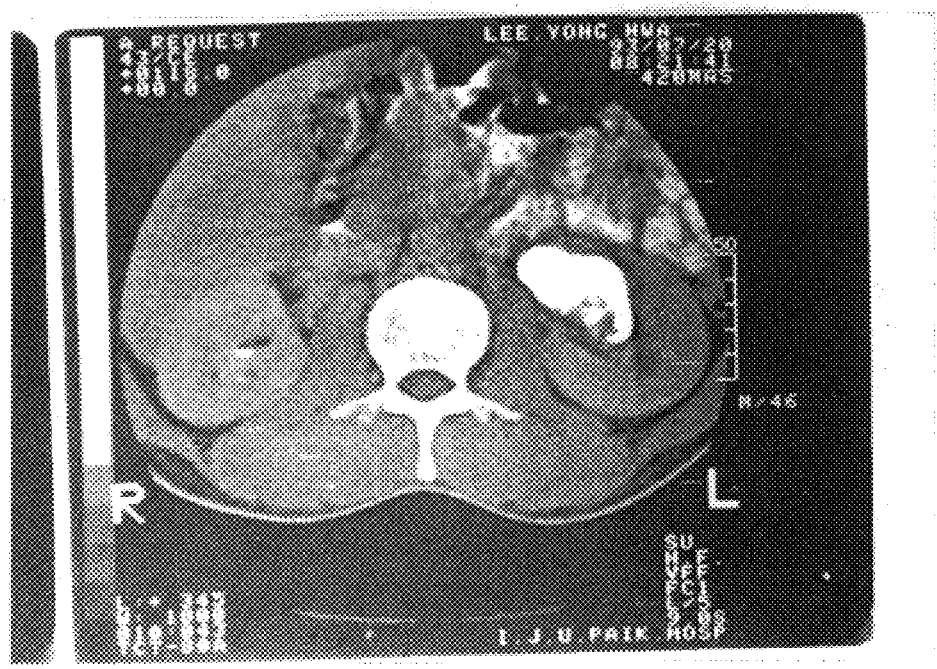
FIG. 47 is a CT scan of a patient with renal carcinoma at terminal stage, demonstrating the same findings as in FIG. 46.
Figure 48:
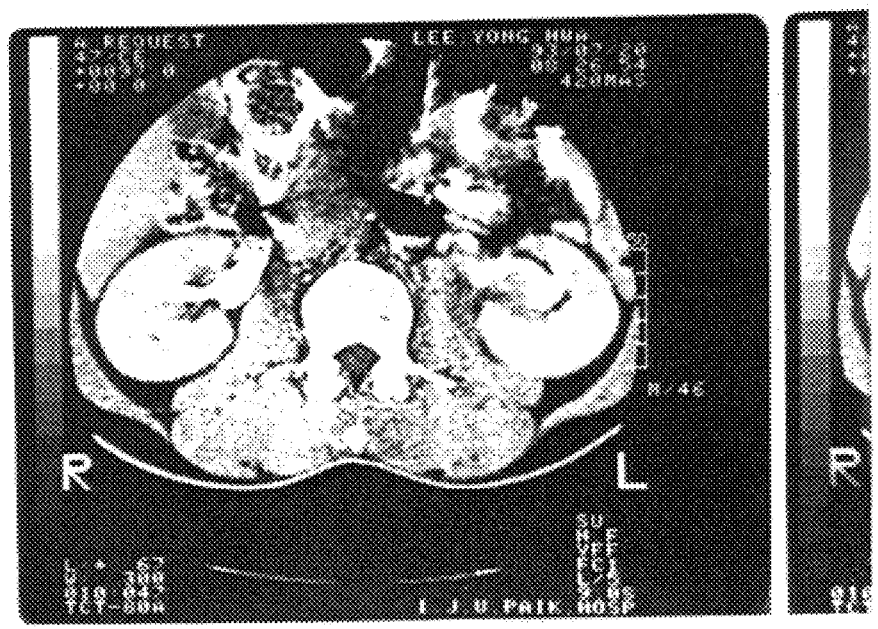
FIG. 48 is a CT scan of a patient with renal carcinoma at terminal stage, demonstrating the same findings as in FIG. 47.
Figure 49:
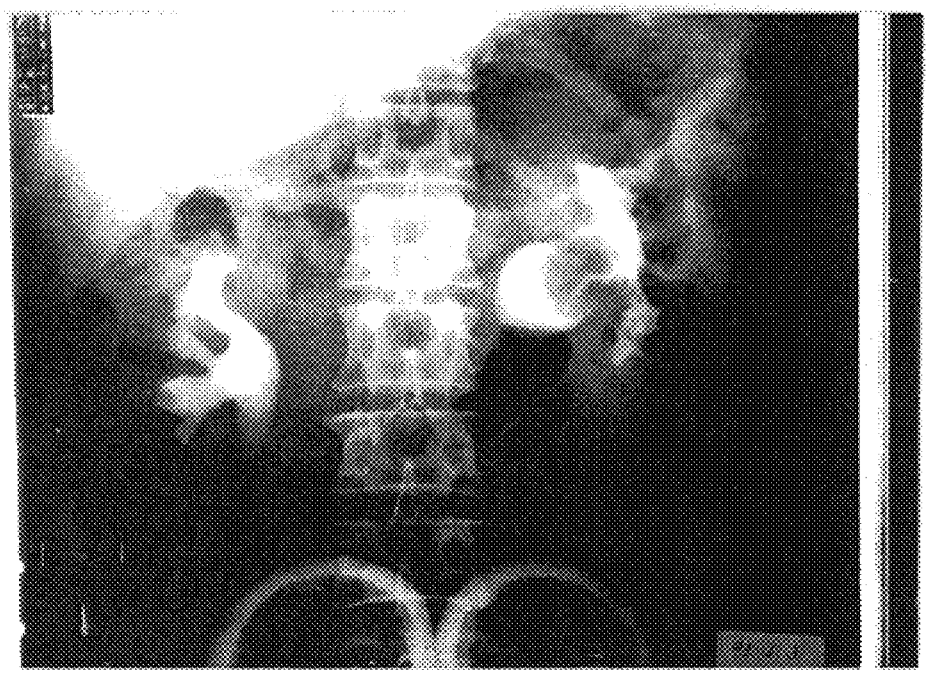
FIG. 49 is a CT scan of a patient with renal carcinoma at terminal stage, showing a marked shrinkage of a cancerous mass in left kidney, following the administration of pharmaceutical composition of $As_4O_6$.
Figure 50:
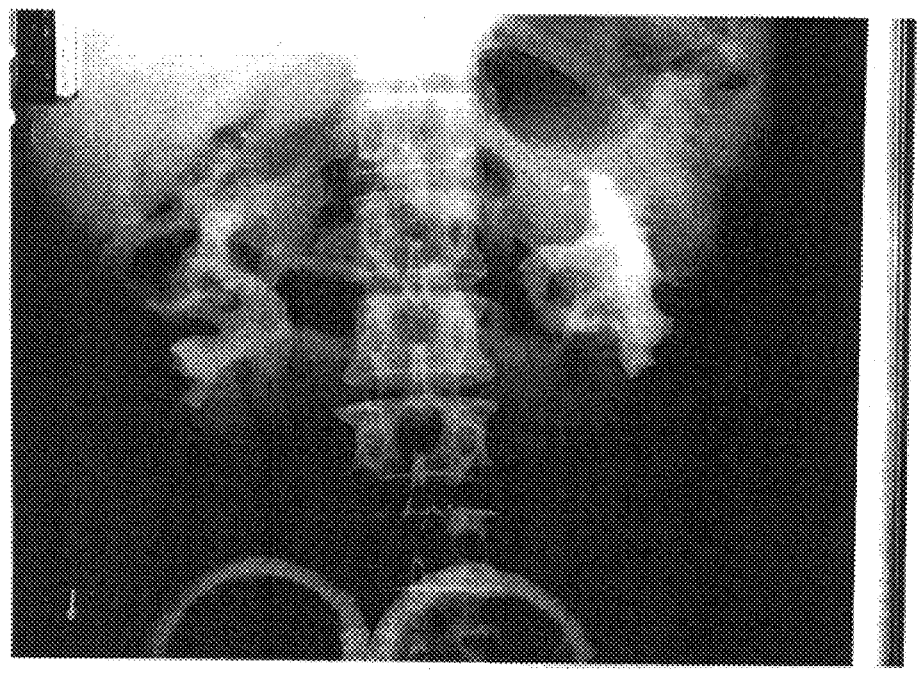
FIG. 50 is a CT scan of a patient with renal carcinoma at terminal stage, showing further shrinkage of tumor mass than in FIG. 49.
Figure 51:
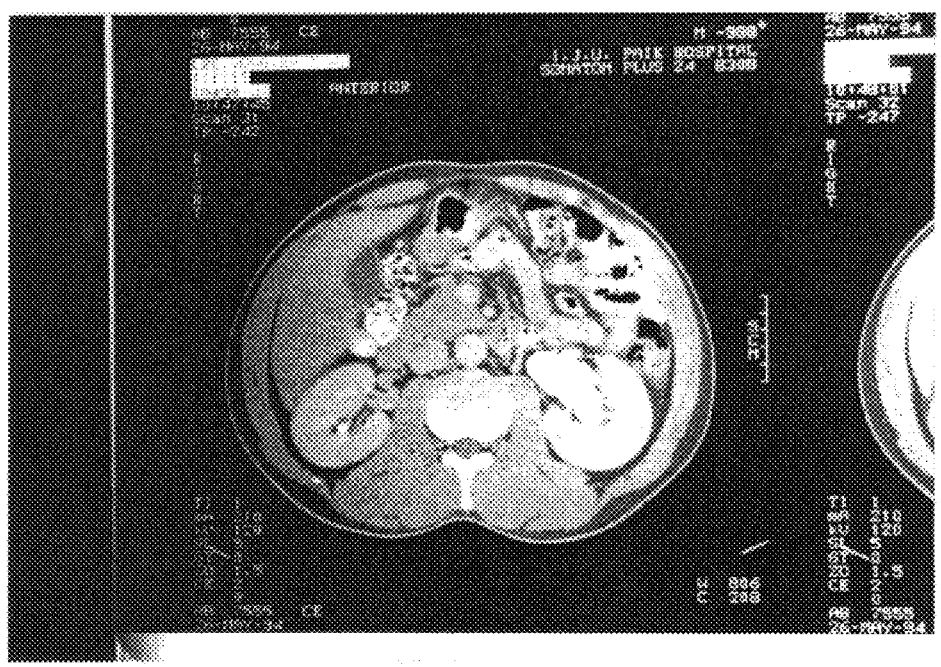
FIG. 51 is a CT scan of a patient with renal carcinoma at terminal stage, showing that white-shadowed contrast material filled the space previously occupied by tumor mass in left kidney.
Figure 52:
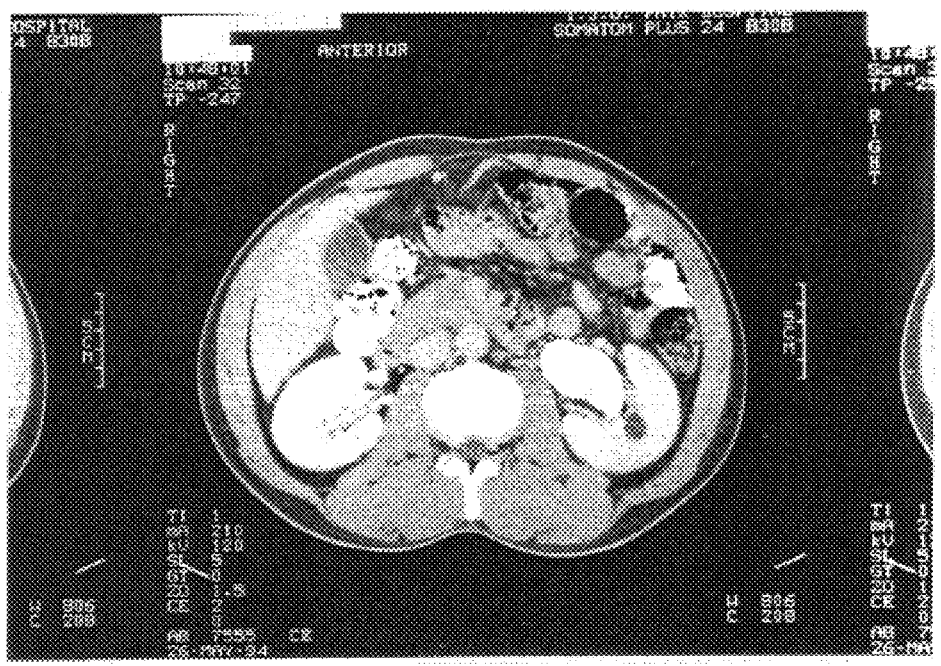
FIG. 52 is a CT scan of a patient with renal carcinoma at terminal stage, showing tiny tumor masses remaining in left kidney and left renal pelvis.
Figure 53:
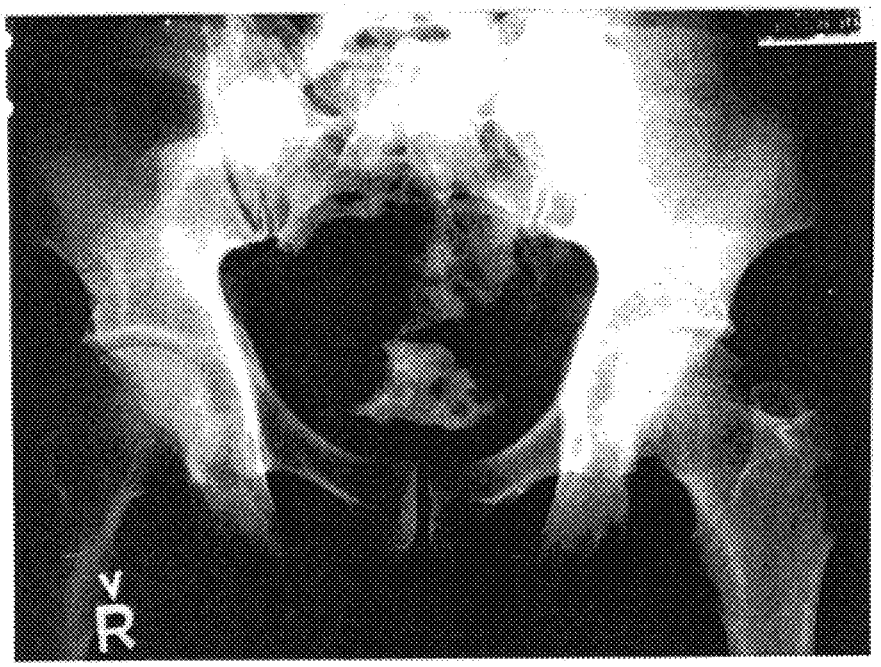
FIG. 53 is a CT scan of a patient with urinary bladder cancer at terminal stage, demonstrating tumor masses in dark shadow, located at the right corner and on the left wall of the urinary bladder.
Figure 54:
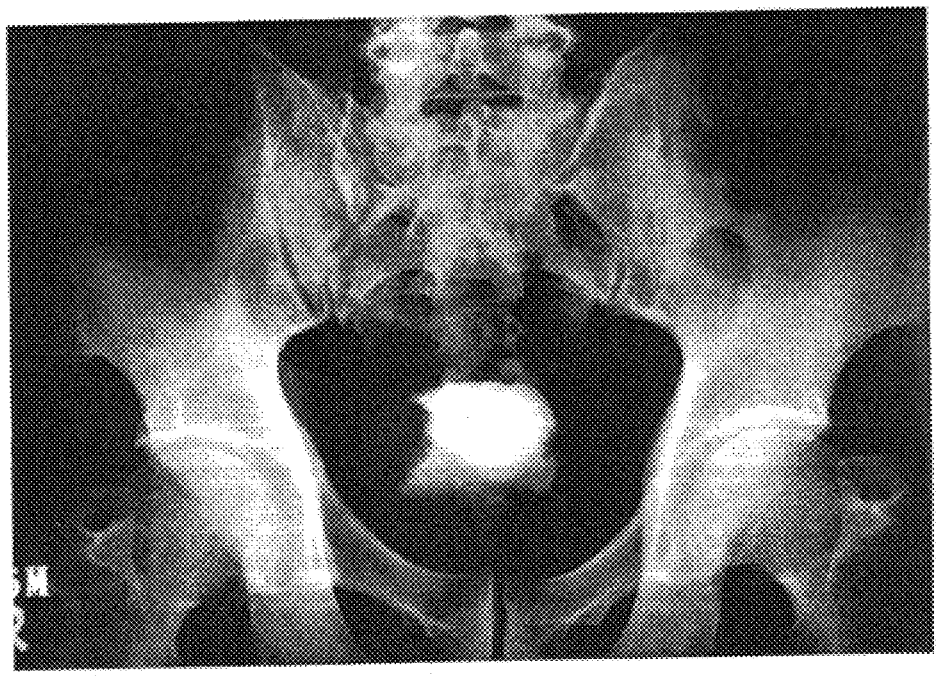
FIG. 54 is a CT scan manifesting the same findings as in FIG. 53.
Figure 55:
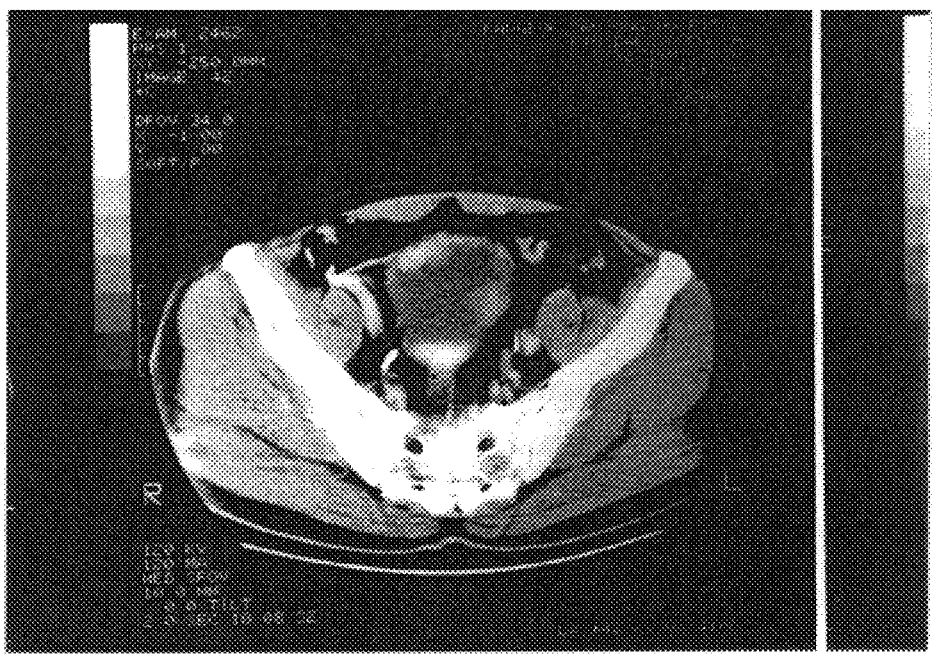
FIG. 55 is a CT scan of a patient with bladder cancer at terminal stage, manifesting the same findings as in FIG. 54, showing a tumor mass in white shadow on left bladder wall.
Figure 56:
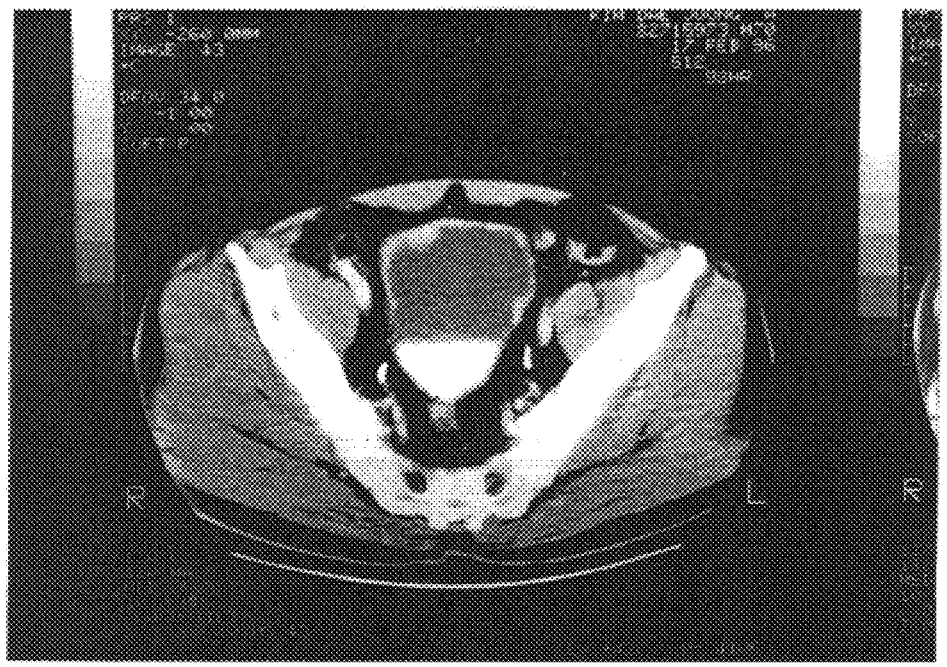
FIG. 56 is a CT scan manifesting the same findings as in FIG. 55.

The study subject (YongHa Lee) was diagnosed of terminal-stage renal cancer at urology department of Pusan Merinol Hospital after thorough examinations including CT scanning. He gave up surgical treatment after being told of low survival rate of 20% even with radical nephrectomy. CT scans taken at dismissal (FIGS. 39 to 44) showed that the left kidney appeared enlarged compared to the right one and left renal pelvis was not filled with contrast material, indicating tumor mass in that region. Intravenous pyelograms were taken after administering tablets prepared as described in EXAMPLE 10. Intravenous pyelograms (FIGS. 45 and 46) indicated marked decrease of tumor mass following 6 months of drug therapy and CT scans (FIG. 47 to 50) demonstrated 80% decrease of tumor mass. Left nephrectomy was done at Pusan Baek Hospital and was confirmed of renal cell carcinoma by pathological examination. With additional administration of tablets as described in 실시예 10 for 3 months, CT scans (FIGS. 51 and 52) demonstrated only tiny tumor mass located in left kidney and renal pelvis, indicating the disease was almost cured.

EXPERIMENT 5

Clinical Trial on a Patient with Urinary Bladder Cancer

Figure 57:
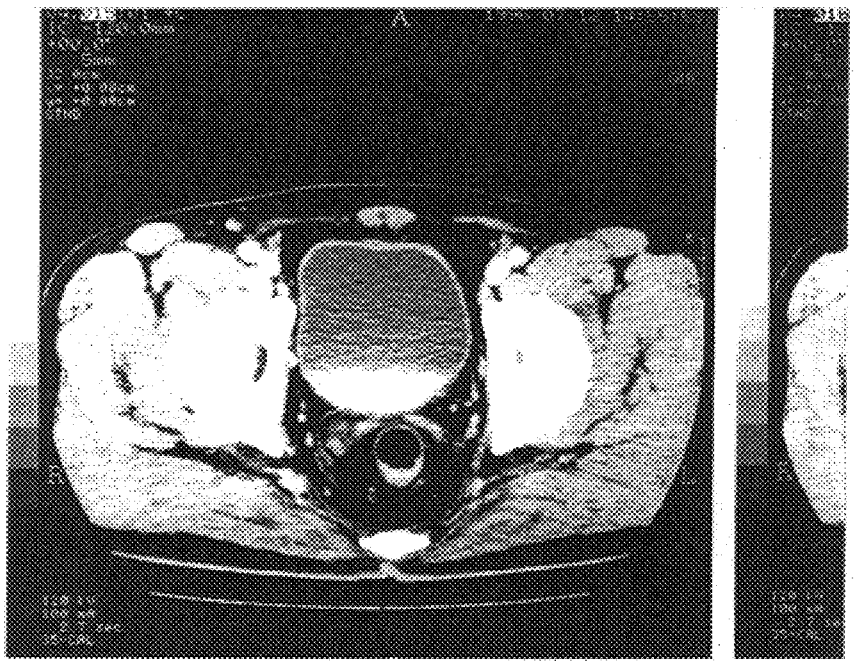
FIG. 57 is a CT scan of a patient with bladder cancer at terminal stage, showing the disappearance of tumor masses following the administration of pharmaceutical composition of $As_4O_6$.
Figure 58:
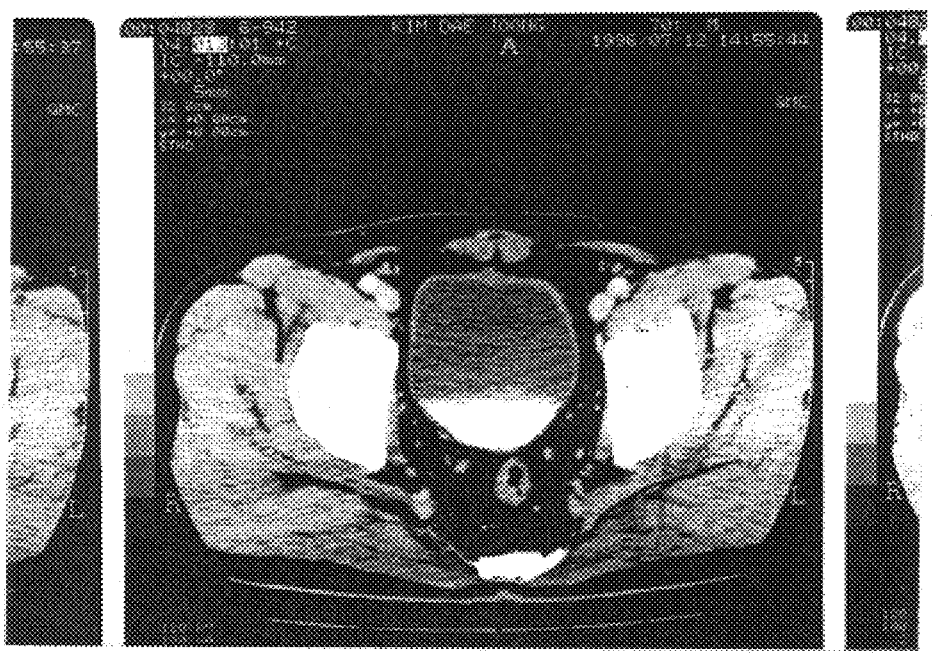
FIG. 58 is a CT scan of a patient with bladder cancer at terminal stage, manifesting the same findings as in FIG. 57.
Figure 59:
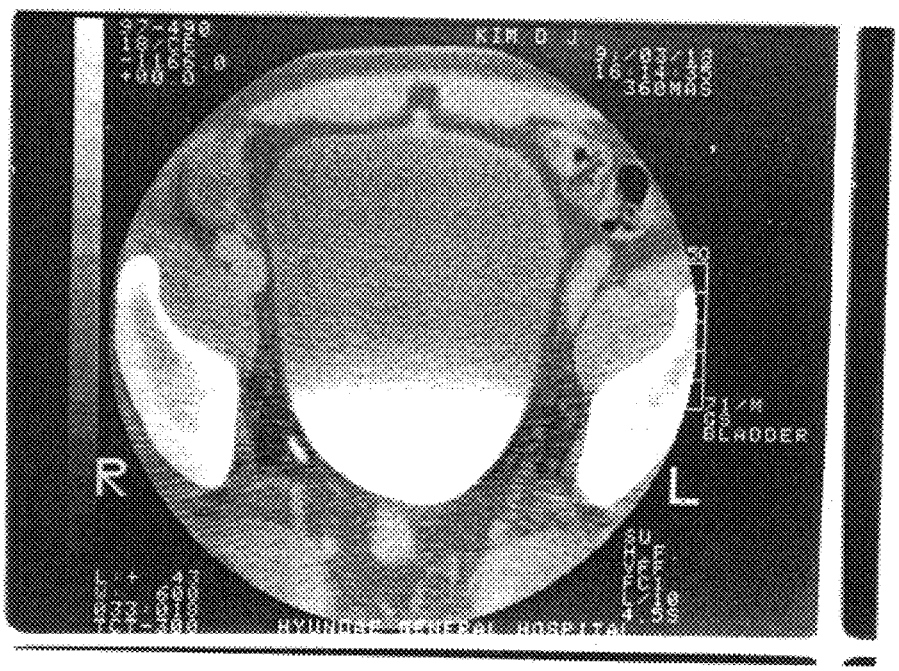
FIG. 59 is a CT scan of a patient with bladder cancer at terminal stage, showing that after treatment, urinary bladder appeared normal.
Figure 60:
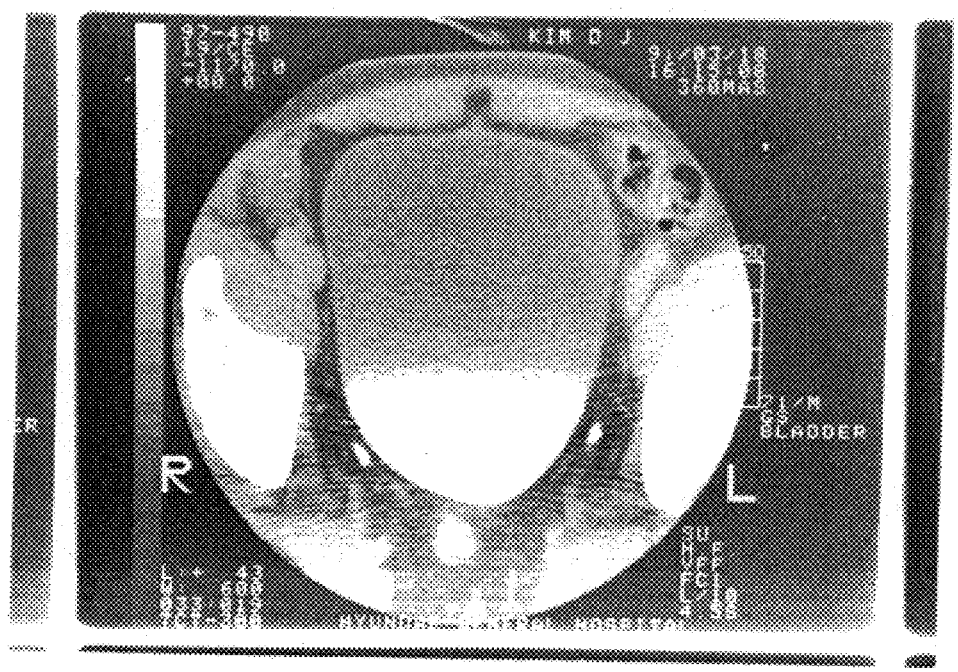
FIG. 60 is a CT scan manifesting the same findings as in FIG. 59.
Figure 61:
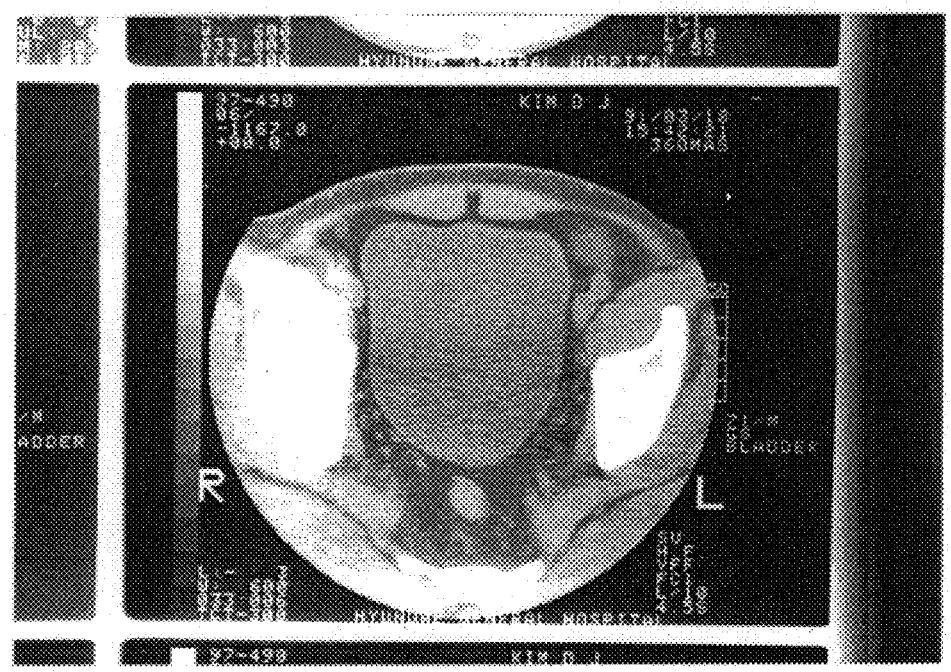
FIG. 61 is a CT scan manifesting the same findings as in FIG. 60.
Figure 62:
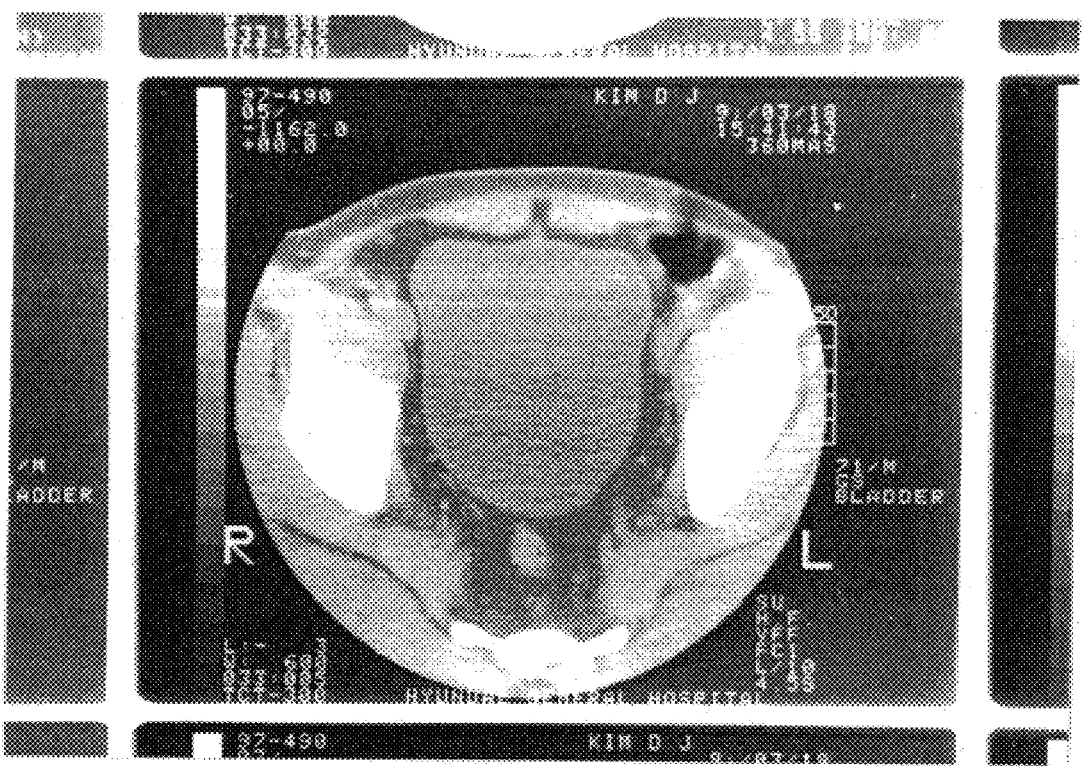
FIG. 62 is a CT scan manifesting the same findings as in FIG. 61.

The study subject (DaeJoong Kim) had been feeling dysuria from June 1995 and was treated for cystitis without any improvement. He was diagnosed of urinary bladder cancer at Samsung Medical Center with thorough examination including CT scanning. With further study at Seoul JoongAng Hospital, CT scans (FIGS. 53 to 56) showed tumor masses in dark shadow on the right corner and left wall of urinary bladder and the survival rate was estimated about 20% within one year. He was treated with tablets prepared as described in EXAMPLE 10 for over 1 year. CT scans (FIGS. 57 and 58), taken at DongIn Hospital of KangNeung on July 1996, indicated no evidence of cancer mass and scans (FIGS. 59 to 62), taken at HyunDae Hospital on Mar. 18, 1997, indicated complete cure of the disease without any shadow of tumor mass.

As shown in EXAMPLES and experiments described above, arsenic hexoxide ($As_4O_6$), which was obtained by separation and purification from a natural material, Sinsuk, had a potent anticancer efficacy in both in vivo and in vitro experiments and inhibited cancer metastasis effectively in animal experiments. Further the natural arsenic compound ($As_4O_6$) was mixed with other ingredients of Oriental medicine to make tablets for oral administration. Clinical trial on cancer patients carrying cancer of uterus, lung, maxillary sinus, kidney, or urinary bladder indicated marked inhibition of proliferation and metastasis of cancer cells following the administration of tablets made from $As_4O_6$. This suggests that the invention could be used as an effective anticancer drug, which may have great impact on the progress of biomedicine.

It will be apparent to those skilled in the art that various modifications and variations can made in an anti-cancer therapy agent of arsenic hexoxide ($As_4O_6$) of a natural chemical substance and its pharmaceutical composition of the present invention without departing from the spirit or scope of the invention. thus, it is intended that the present invention cover the modifications and variations of this invention provided they come within the scope of the appended claims and their equivalents.

What is claimed is:

1. A pharmaceutical composition, comprising
   a pharmaceutically effective amount of $As_4O_6$ and a pharmaceutically effective carrier, wherein said $As_4O_6$ is naturally derived from Sinsuk.

* * * * *